United States Patent
Hoffer et al.

(10) Patent No.: US 11,311,730 B2
(45) Date of Patent: *Apr. 26, 2022

(54) SYSTEMS AND RELATED METHODS FOR OPTIMIZATION OF MULTI-ELECTRODE NERVE PACING

(71) Applicant: Lungpacer Medical Inc., Vancouver (CA)

(72) Inventors: Joaquin Andres Hoffer, Anmore (CA); Gautam Sadarangani, Burnaby (CA); Marc-Andre Nolette, Burnaby (CA); Viral S. Thakkar, Chester Springs, PA (US); Bao Dung Tran, Vancouver (CA)

(73) Assignee: Lungpacer Medical Inc., Burnaby (CA)

( * ) Notice: Subject to any disclaimer, the term of this patent is extended or adjusted under 35 U.S.C. 154(b) by 314 days.

This patent is subject to a terminal disclaimer.

(21) Appl. No.: 16/510,403

(22) Filed: Jul. 12, 2019

(65) Prior Publication Data

US 2019/0336773 A1 Nov. 7, 2019

Related U.S. Application Data

(63) Continuation of application No. 15/427,924, filed on Feb. 8, 2017, now Pat. No. 10,391,314, which is a (Continued)

(51) Int. Cl.
*A61N 1/36* (2006.01)
*A61N 1/05* (2006.01)
(Continued)

(52) U.S. Cl.
CPC ........ *A61N 1/36185* (2013.01); *A61B 5/0205* (2013.01); *A61B 5/4836* (2013.01);
(Continued)

(58) Field of Classification Search
None
See application file for complete search history.

(56) References Cited

U.S. PATENT DOCUMENTS

| 1,693,734 A | 12/1928 | Waggoner |
| 2,532,788 A | 12/1950 | Sarnoff |

(Continued)

FOREIGN PATENT DOCUMENTS

| CN | 1652839 A | 8/2005 |
| CN | 102143781 A | 8/2011 |

(Continued)

OTHER PUBLICATIONS

Pavlovic, D. et al, "Diaphragm pacing during prolonged mechanical ventilation of the lungs could prevent from respiratory muscle fatigue", Medical Hypotheses, 2003, vol. 60, No. 3, pp. 398-403.

(Continued)

*Primary Examiner* — Michael W Kahelin
(74) *Attorney, Agent, or Firm* — Bookoff McAndrews, PLLC

(57) ABSTRACT

This disclosure describes, among other embodiments, systems and related methods for selecting electrode combinations to be used during nerve pacing procedures. A first set of electrode combinations of a nerve pacing system, such as a phrenic nerve pacing system for diaphragm activation, may be mapped (or tested) to determine the location of the electrode combinations relative to a target nerve. Once the general location of the target nerve is known, a more localized second set of electrode combinations may be tested to determine the most suitable electrode combinations for nerve stimulation. At various stages of the mapping process, electrode combinations that are non-optimal may be discarded as candidates for use in a nerve pacing procedure. The systems and methods described herein may allow for the selection of electrode combinations that are most suit- (Continued)

able for stimulation of the left and right phrenic nerves during diaphragm pacing.

33 Claims, 16 Drawing Sheets

Related U.S. Application Data continuation of application No. 15/095,773, filed on Apr. 11, 2016, now Pat. No. 9,597,509, which is a continuation of application No. 14/600,763, filed on Jan. 20, 2015, now Pat. No. 9,333,363.

(60) Provisional application No. 61/929,901, filed on Jan. 21, 2014.

(51) Int. Cl.
| | |
|---|---|
| A61B 5/0205 | (2006.01) |
| A61B 5/00 | (2006.01) |
| A61B 5/0245 | (2006.01) |
| A61B 5/05 | (2021.01) |
| A61B 5/08 | (2006.01) |
| A61B 5/145 | (2006.01) |
| A61B 5/24 | (2021.01) |
| A61B 5/287 | (2021.01) |
| A61B 5/389 | (2021.01) |

(52) U.S. Cl.
CPC .......... *A61B 5/4893* (2013.01); *A61B 5/6852* (2013.01); *A61B 5/7264* (2013.01); *A61N 1/0551* (2013.01); *A61N 1/3611* (2013.01); *A61N 1/36139* (2013.01); *A61B 5/0245* (2013.01); *A61B 5/05* (2013.01); *A61B 5/08* (2013.01); *A61B 5/145* (2013.01); *A61B 5/24* (2021.01); *A61B 5/287* (2021.01); *A61B 5/389* (2021.01); *A61B 5/4818* (2013.01); *A61B 2562/043* (2013.01)

(56) References Cited

U.S. PATENT DOCUMENTS

| | | |
|---|---|---|
| 2,664,880 A | 1/1954 | Wales, Jr. |
| 3,348,548 A | 10/1967 | Chardack |
| 3,470,876 A | 10/1969 | Barchilon |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | McCormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | LaFontaine et al. |
| 5,678,535 A | 10/1997 | DiMarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |

(56) References Cited

U.S. PATENT DOCUMENTS

| | | |
|---|---|---|
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | McDaniel |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van Venrooij et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kass et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |

(56) References Cited

U.S. PATENT DOCUMENTS

| | | | |
|---|---|---|---|
| 8,321,808 | B2 | 11/2012 | Goetz et al. |
| 8,335,567 | B2 | 12/2012 | Tehrani et al. |
| 8,340,783 | B2 | 12/2012 | Sommer et al. |
| 8,348,941 | B2 | 1/2013 | Tehrani |
| 8,369,954 | B2 | 2/2013 | Stack et al. |
| 8,374,704 | B2 | 2/2013 | Desai et al. |
| 8,388,541 | B2 | 3/2013 | Messerly et al. |
| 8,388,546 | B2 | 3/2013 | Rothenberg |
| 8,391,956 | B2 | 3/2013 | Zellers et al. |
| 8,401,640 | B2 | 3/2013 | Zhao et al. |
| 8,401,651 | B2 | 3/2013 | Caparso et al. |
| 8,406,883 | B1 | 3/2013 | Barker |
| 8,406,885 | B2 | 3/2013 | Ignagni et al. |
| 8,412,331 | B2 | 4/2013 | Tehrani et al. |
| 8,412,350 | B2 | 4/2013 | Bly |
| 8,428,711 | B2 | 4/2013 | Lin et al. |
| 8,428,726 | B2 | 4/2013 | Ignagni et al. |
| 8,428,730 | B2 | 4/2013 | Stack et al. |
| 8,433,412 | B1 | 4/2013 | Westlund et al. |
| 8,442,638 | B2 | 5/2013 | Libbus et al. |
| 8,457,764 | B2 | 6/2013 | Ramachandran et al. |
| 8,467,876 | B2 | 6/2013 | Tehrani |
| 8,473,068 | B2 | 6/2013 | Farazi |
| 8,478,412 | B2 | 7/2013 | Ignagni et al. |
| 8,478,413 | B2 | 7/2013 | Karamanoglu et al. |
| 8,478,426 | B2 | 7/2013 | Barker |
| 8,483,834 | B2 | 7/2013 | Lee et al. |
| 8,504,158 | B2 | 8/2013 | Karamanoglu et al. |
| 8,504,161 | B1 | 8/2013 | Kornet et al. |
| 8,509,901 | B2 | 8/2013 | Tehrani |
| 8,509,902 | B2 | 8/2013 | Cho et al. |
| 8,509,919 | B2 | 8/2013 | Yoo et al. |
| 8,512,256 | B2 | 8/2013 | Rothenberg |
| 8,522,779 | B2 | 9/2013 | Lee et al. |
| 8,527,036 | B2 | 9/2013 | Jalde et al. |
| 8,532,793 | B2 | 9/2013 | Morris et al. |
| 8,554,323 | B2 | 10/2013 | Haefner et al. |
| 8,560,072 | B2 | 10/2013 | Caparso et al. |
| 8,560,086 | B2 | 10/2013 | Just et al. |
| 8,571,662 | B2 | 10/2013 | Hoffer |
| 8,571,685 | B2 | 10/2013 | Daglow et al. |
| 8,615,297 | B2 | 12/2013 | Sathaye et al. |
| 8,617,228 | B2 | 12/2013 | Wittenberger et al. |
| 8,620,412 | B2 | 12/2013 | Griffiths et al. |
| 8,620,450 | B2 | 12/2013 | Tockman et al. |
| 8,626,292 | B2 | 1/2014 | McCabe et al. |
| 8,630,707 | B2 | 1/2014 | Zhao et al. |
| 8,644,939 | B2 | 2/2014 | Wilson et al. |
| 8,644,952 | B2 | 2/2014 | Desai et al. |
| 8,646,172 | B2 | 2/2014 | Kuzma et al. |
| 8,650,747 | B2 | 2/2014 | Kuzma et al. |
| 8,676,323 | B2 | 3/2014 | Ignagni et al. |
| 8,676,344 | B2 | 3/2014 | Desai et al. |
| 8,694,123 | B2 | 4/2014 | Wahlstrand et al. |
| 8,696,656 | B2 | 4/2014 | Abboud et al. |
| 8,706,223 | B2 | 4/2014 | Zhou et al. |
| 8,706,235 | B2 | 4/2014 | Karamanoglu et al. |
| 8,706,236 | B2 | 4/2014 | Ignagni et al. |
| 8,718,763 | B2 | 5/2014 | Zhou et al. |
| 8,725,259 | B2 | 5/2014 | Kornet et al. |
| 8,738,154 | B2 | 5/2014 | Zdeblick et al. |
| 8,755,889 | B2 | 6/2014 | Scheiner |
| 8,774,907 | B2 | 7/2014 | Rothenberg |
| 8,781,578 | B2 | 7/2014 | McCabe et al. |
| 8,781,582 | B2 | 7/2014 | Ziegler et al. |
| 8,781,583 | B2 | 7/2014 | Cornelussen et al. |
| 8,801,693 | B2 | 8/2014 | He et al. |
| 8,805,511 | B2 | 8/2014 | Karamanoglu et al. |
| 8,838,245 | B2 | 9/2014 | Lin et al. |
| 8,858,455 | B2 | 10/2014 | Rothenberg |
| 8,863,742 | B2 | 10/2014 | Blomquist et al. |
| 8,886,277 | B2 | 11/2014 | Kim et al. |
| 8,897,879 | B2 | 11/2014 | Karamanoglu et al. |
| 8,903,507 | B2 | 12/2014 | Desai et al. |
| 8,903,509 | B2 | 12/2014 | Tockman et al. |
| 8,909,341 | B2 | 12/2014 | Gelfand et al. |
| 8,914,113 | B2 | 12/2014 | Zhang et al. |
| 8,918,169 | B2 | 12/2014 | Kassab et al. |
| 8,918,987 | B2 | 12/2014 | Kuzma et al. |
| 8,923,971 | B2 | 12/2014 | Haefner et al. |
| 8,942,823 | B2 | 1/2015 | Desai et al. |
| 8,942,824 | B2 | 1/2015 | Yoo et al. |
| 8,948,884 | B2 | 2/2015 | Ramachandran et al. |
| 8,968,299 | B2 | 3/2015 | Kauphusman et al. |
| 8,972,015 | B2 | 3/2015 | Stack et al. |
| 8,983,602 | B2 | 3/2015 | Sathaye et al. |
| 9,008,775 | B2 | 4/2015 | Sathaye et al. |
| 9,026,231 | B2 | 5/2015 | Hoffer |
| 9,037,264 | B2 | 5/2015 | Just et al. |
| 9,042,981 | B2 | 5/2015 | Yoo et al. |
| 9,072,864 | B2 | 7/2015 | Putz |
| 9,072,899 | B1 | 7/2015 | Nickloes |
| 9,108,058 | B2 | 8/2015 | Hoffer |
| 9,108,059 | B2 | 8/2015 | Hoffer |
| 9,125,578 | B2 | 9/2015 | Grunwald |
| 9,138,580 | B2 | 9/2015 | Ignagni et al. |
| 9,138,585 | B2 | 9/2015 | Saha et al. |
| 9,149,642 | B2 | 10/2015 | McCabe et al. |
| 9,168,377 | B2 | 10/2015 | Hoffer |
| 9,205,258 | B2 | 12/2015 | Simon et al. |
| 9,216,291 | B2 | 12/2015 | Lee et al. |
| 9,220,898 | B2 | 12/2015 | Hoffer |
| 9,226,688 | B2 | 1/2016 | Jacobsen et al. |
| 9,226,689 | B2 | 1/2016 | Jacobsen et al. |
| 9,242,088 | B2 | 1/2016 | Thakkar et al. |
| 9,259,573 | B2 | 2/2016 | Tehrani et al. |
| 9,295,846 | B2 | 3/2016 | Westlund et al. |
| 9,314,618 | B2 | 4/2016 | Imran et al. |
| 9,333,363 | B2 | 5/2016 | Hoffer et al. |
| 9,345,422 | B2 | 5/2016 | Rothenberg |
| 9,370,657 | B2 | 6/2016 | Tehrani et al. |
| 9,398,931 | B2 | 7/2016 | Wittenberger et al. |
| 9,415,188 | B2 | 8/2016 | He et al. |
| 9,427,566 | B2 | 8/2016 | Reed et al. |
| 9,427,588 | B2 | 8/2016 | Sathaye et al. |
| 9,474,894 | B2 | 10/2016 | Mercanzini et al. |
| 9,485,873 | B2 | 11/2016 | Shah et al. |
| 9,498,625 | B2 | 11/2016 | Bauer et al. |
| 9,498,631 | B2 | 11/2016 | Demmer et al. |
| 9,504,837 | B2 | 11/2016 | Demmer et al. |
| 9,532,724 | B2 | 1/2017 | Grunwald et al. |
| 9,533,160 | B2 | 1/2017 | Brooke et al. |
| 9,539,429 | B2 | 1/2017 | Brooke et al. |
| 9,545,511 | B2 | 1/2017 | Thakkar et al. |
| 9,561,369 | B2 | 2/2017 | Burnes et al. |
| 9,566,436 | B2 | 2/2017 | Hoffer et al. |
| 9,572,982 | B2 | 2/2017 | Burnes et al. |
| 9,597,509 | B2 | 3/2017 | Hoffer et al. |
| 9,615,759 | B2 | 4/2017 | Hurezan et al. |
| 9,623,252 | B2 | 4/2017 | Sathaye et al. |
| 9,662,494 | B2 | 5/2017 | Young et al. |
| 9,682,235 | B1 | 6/2017 | O'Mahony et al. |
| 9,694,185 | B2 | 7/2017 | Bauer |
| 9,717,899 | B2 | 8/2017 | Kuzma et al. |
| 9,724,018 | B2 | 8/2017 | Cho et al. |
| 9,744,351 | B1 | 8/2017 | Gelfand et al. |
| 9,776,005 | B2 | 10/2017 | Meyyappan et al. |
| 9,861,817 | B2 | 1/2018 | Cho et al. |
| 9,872,989 | B2 | 1/2018 | Jung et al. |
| 9,884,178 | B2 | 2/2018 | Bouton et al. |
| 9,884,179 | B2 | 2/2018 | Bouton et al. |
| 9,919,149 | B2 | 3/2018 | Imran et al. |
| 9,931,504 | B2 | 4/2018 | Thakkar et al. |
| 9,950,167 | B2 | 4/2018 | Hoffer et al. |
| 9,956,396 | B2 | 5/2018 | Young et al. |
| 9,968,785 | B2 | 5/2018 | Hoffer et al. |
| 9,968,786 | B2 | 5/2018 | Bauer et al. |
| 2001/0052345 | A1 | 12/2001 | Niazi |
| 2002/0026228 | A1 | 2/2002 | Schauerte |
| 2002/0056454 | A1 | 5/2002 | Samzelius |
| 2002/0065544 | A1 | 5/2002 | Smits et al. |
| 2002/0087156 | A1 | 7/2002 | Maguire et al. |
| 2002/0128546 | A1 | 9/2002 | Silver |
| 2002/0188325 | A1 | 12/2002 | Hill et al. |

(56) References Cited

U.S. PATENT DOCUMENTS

| | | |
|---|---|---|
| 2003/0078623 A1 | 4/2003 | Weinberg et al. |
| 2003/0195571 A1 | 10/2003 | Burnes et al. |
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | McCreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0224209 A1 | 10/2006 | Meyer |
| 2006/0224222 A1* | 10/2006 | Bradley .............. A61N 1/36071 607/116 |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2010/0022950 A1 | 1/2010 | Anderson et al. |
| 2010/0036451 A1 | 2/2010 | Hoffer |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0060381 A1 | 3/2011 | Ignagni et al. |
| 2011/0077726 A1 | 3/2011 | Westlund et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1* | 11/2011 | Tehrani .............. A61N 1/36031 607/42 |
| 2012/0035684 A1 | 2/2012 | Thompson et al. |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0116743 A1 | 5/2013 | Karamanoglu et al. |

(56) References Cited

U.S. PATENT DOCUMENTS

| | | |
|---|---|---|
| 2013/0123891 A1 | 5/2013 | Swanson |
| 2013/0131743 A1 | 5/2013 | Yamasaki et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De La Rama et al. |
| 2015/0374991 A1 | 12/2015 | Morris et al. |
| 2016/0001072 A1 | 1/2016 | Gelfand et al. |
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | McFarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |

FOREIGN PATENT DOCUMENTS

| | | |
|---|---|---|
| EP | 0993840 A1 | 4/2000 |
| EP | 1304135 A2 | 4/2003 |
| EP | 0605796 B1 | 8/2003 |
| EP | 2489395 A1 | 8/2012 |
| FR | 2801509 A1 | 6/2001 |
| JP | H08510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | 9407564 A2 | 4/1994 |
| WO | 9508357 A1 | 3/1995 |
| WO | 9964105 A1 | 12/1999 |
| WO | 9965561 A1 | 12/1999 |
| WO | 0100273 A1 | 1/2001 |
| WO | 02058785 A1 | 8/2002 |
| WO | 03/005887 A2 | 1/2003 |
| WO | 03094855 A1 | 11/2003 |
| WO | 2006110338 A1 | 10/2006 |
| WO | 2006115877 A1 | 11/2006 |
| WO | 2007053508 A1 | 5/2007 |
| WO | 2008/092246 A1 | 8/2008 |
| WO | 2008094344 A1 | 8/2008 |
| WO | 2009006337 A1 | 1/2009 |
| WO | 2009134459 A2 | 11/2009 |
| WO | 2010029842 A1 | 3/2010 |
| WO | 2010148412 A1 | 12/2010 |
| WO | 2011158410 A1 | 12/2011 |
| WO | 2012106533 A2 | 8/2012 |
| WO | 2013131187 A1 | 9/2013 |
| WO | 2013/188965 A1 | 12/2013 |

OTHER PUBLICATIONS

Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.

Wanner, A. et al., "Trasvenous Phrenic Nerve Stimulation in Anesthetized Dogs," Journal of Applied Physiology, 1973, vol. 34 (4), pp. 489-494.

Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.

Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.

Whaley K., et al., "C2 Synthesis by Human Monocytes is Modulated by a Nicotinic Cholinergic Receptor," Nature, vol. 293, Oct. 15, 1981, pp. 580-582 (and reference page).

Extended European Search Report issued in corresponding EP Application No. 19182380.6 dated Sep. 18, 2019.

Antonica A., et al., "Vagal Control of Lymphocyte Release from Rat Thymus," Journal of the Autonomic Nervous System, Elsevier, vol. 48(3), Aug. 1994, pp. 187-197.

Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikova, et al., "Role of the Vagus Nerve in the Anti-Inflammatory Effects of CNI-1493," Proceedings of the Annual Meeting of Professional Research Scientists: Experimental Biology 2000, Abstract 97.9, Apr. 15-18, 2000.

Borovikovaa L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.

Borovikovaa L.V., et al., "Vagus Nerve Stimulation Attenuates the Systemic Inflammatory Response to Endotoxin," Nature, Macmillan Magazines Ltd, vol. 405, May 25, 2000, pp. 458-462.

Chinese Search Report for Application No. CN2013/80023357.5, dated Jul. 24, 2015.

Co-pending U.S. Appl. No. 15/606,867, filed May 26, 2017.

(56) References Cited

OTHER PUBLICATIONS

Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.

Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.

De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.

Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.

European Search Report for Application No. 13758363, dated Nov. 12, 2015.

European Search Report for Application No. EP17169051.4, dated Sep. 8, 2017, 7 pages.

Extended European Search Report for Application No. 14864542.7, dated Jun. 2, 2017, 8 pages.

Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.

Frisch S., "A Feasibility Study of a Novel Minimally Invasive Approach for Diaphragm Pacing," Master of Science Thesis, Simon Fraser University, 2009, p. 148.

Furman, S., "Transvenous Stimulation of the Phrenic Nerves," Journal of Thoracic and Cardiovascular Surgery, 1971, vol. 62 (5), pp. 743-751.

Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.

Gupta A.K., "Respiration Rate Measurement Based on Impedance Pneumography," Data Acquisition Products, Texas Instruments, Application Report, SBAA181, Feb. 2011, 11 pages.

Guslandi M., "Nicotine Treatment for Ulcerative Colitis," The British Journal of Clinical Pharmacology, Blackwell Science Ltd, vol. 48, 1999, pp. 481-484.

Hoffer J.A. et al., "Diaphragm Pacing with Endovascular Electrodes", IFESS 2010—International Functional Electrical Stimulation Society, 15th Anniversary Conference, Vienna, Austria, Sep. 2010.

Japanese Office Action in corresponding Japanese Application No. 2014-560202, dated Dec. 6, 2016, 4 pages.

Japanese Office Action in corresponding Japanese Application No. 2014-560202, dated Oct. 17, 2017, 5 pages.

Kawashima K., et al., "Extraneuronal Cholinergic System in Lymphocytes," Pharmacology & Therapeutics, Elsevier, vol. 86, 2000, pp. 29-48.

Levine S., et al., "Rapid disuse atrophy of diaphragm fibers in mechanically ventilated humans," New England Journal of Medicine, 2008, vol. 358, pp. 1327-1335.

Lungpacer: Therapy, News. . Accessed Dec. 27, 2016.

Madretsma, G.S., et al., "Nicotine Inhibits the In-vitro Production of Interleukin 2 and Tumour Necrosis Factor-α by Human Mononuclear Cells," Immunopharmacology, Elsevier, vol. 35 (1), Oct. 1996, pp. 47-51.

Marcy, T.W. et al., "Diaphragm Pacing for Ventilatory Insufficiency," Journal of Intensive Care Medicine, 1987, vol. 2 (6), pp. 345-353.

Meyyappan R., "Diaphragm Pacing during Controlled Mechanical Ventilation: Pre-Clinical Observations Reveal a Substantial Improvement in Respiratory Mechanics", 17th Biennial Canadian Biomechanics Society Meeting, Burnaby, BC, Jun. 6-9, 2012.

Nabutovsky, Y., et al., "Lead Design and Initial Applications of a New Lead for Long-Term Endovascular Vagal Stimulation," PACE, Blackwell Publishing, Inc, vol. 30(1), Jan. 2007, pp. S215-S218.

Notification of Reasons for Rejection and English language translation issued in corresponding Japanese Patent Application No. 2015-517565, dated Mar. 28, 2017, 6 pages.

Onders R.,, "A Diaphragm Pacing as a Short-Term Assist to Positive Pressure Mechanical Ventilation in Critical Care Patients," Chest, Oct. 24, 2007, vol. 132(4), pp. 5715-5728.

Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.

Onders R, et al., "Diaphragm Pacing with Natural Orifice Transluminal Endoscopic Surgery: Potential for Difficult-to-Wean Intensive Care Unit Patients," Surgical Endoscopy, 2007, vol. 21, pp. 475-479.

Planas R.F., et al., "Diaphragmatic Pressures: Transvenous vs. Direct Phrenic Nerve Stimulation," Journal of Applied Physiology, vol. 59(1), 1985, pp. 269-273.

Romanovsky, A.A., et al., "The Vagus Nerve in the Thermoregulatory Response to Systemic Inflammation," American Journal of Physiology, vol. 273 (1 Pt 2), 1997, pp. R407-R413.

Salmela L., et al., "Verification of the Position of a Central Venous Catheter by Intra-Atrial ECG. When does this method fail?," Acta Anasthesiol Scand, vol. 37 (1), 1993, pp. 26-28.

Sandborn W.J., "Transdermal Nicotine for Mildly to Moderately Active Ulcerative Colitis," Annals of Internal Medicine, vol. 126 (5), Mar. 1, 1997, pp. 364-371.

Sandoval R., "A Catch/Ike Property-Based Stimulation Protocol for Diaphragm Pacing", Master of Science Coursework project, Simon Fraser University, Mar. 2013.

Sarnoff, S.J. et al., "Electrophrenic Respiration," Science, 1948, vol. 108, p. 482.

Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.

Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.

Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.

Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.

Scheinman R.I., et al., "Role of Transcriptional Activation of IκBα in Mediation of Immunosuppression by Glucocorticoids," Science, vol. 270, Oct. 13, 1995, pp. 283-286.

Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.

Steinlein, O., "New Functions for Nicotinic Acetylcholine Receptors?," Behavioural Brain Research, vol. 95, 1998, pp. 31-35.

Sternberg E.M., (Series Editor) "Neural-Immune Interactions in Health and Disease," The Journal of Clinical Investigation, vol. 100 (11), Dec. 1997, pp. 2641-2647.

Sykes., A.P., et al., "An Investigation into the Effect and Mechanisms of Action of Nicotine in Inflammatory Bowel Disease," Inflammation Research, vol. 49, 2000, pp. 311-319.

Toyabe S., et al., "Identification of Nicotinic Acetylcholine Receptors on Lymphocytes in the Periphery as well as Thymus in Mice," Immunology, vol. 92, 1997, pp. 201-205.

Extended European Search Report dated Jul. 7, 2017 in related European Application No. 15740415.3.

Escher, Doris J.W. et al., "Clinical Control of Respiration by Transvenous Phrenic Pacing," American Society for Artificial Internal Organs: Apr. 1968—vol. 14—Issue 1—pp. 192-197.

(56) References Cited

OTHER PUBLICATIONS

Ishii, K. et al., "Effects of Bilateral Transvenous Diaphragm Pacing on Hemodynamic Function in Patients after Cardiac Operations," J. Thorac. Cardiovasc. Surg., 1990.

* cited by examiner

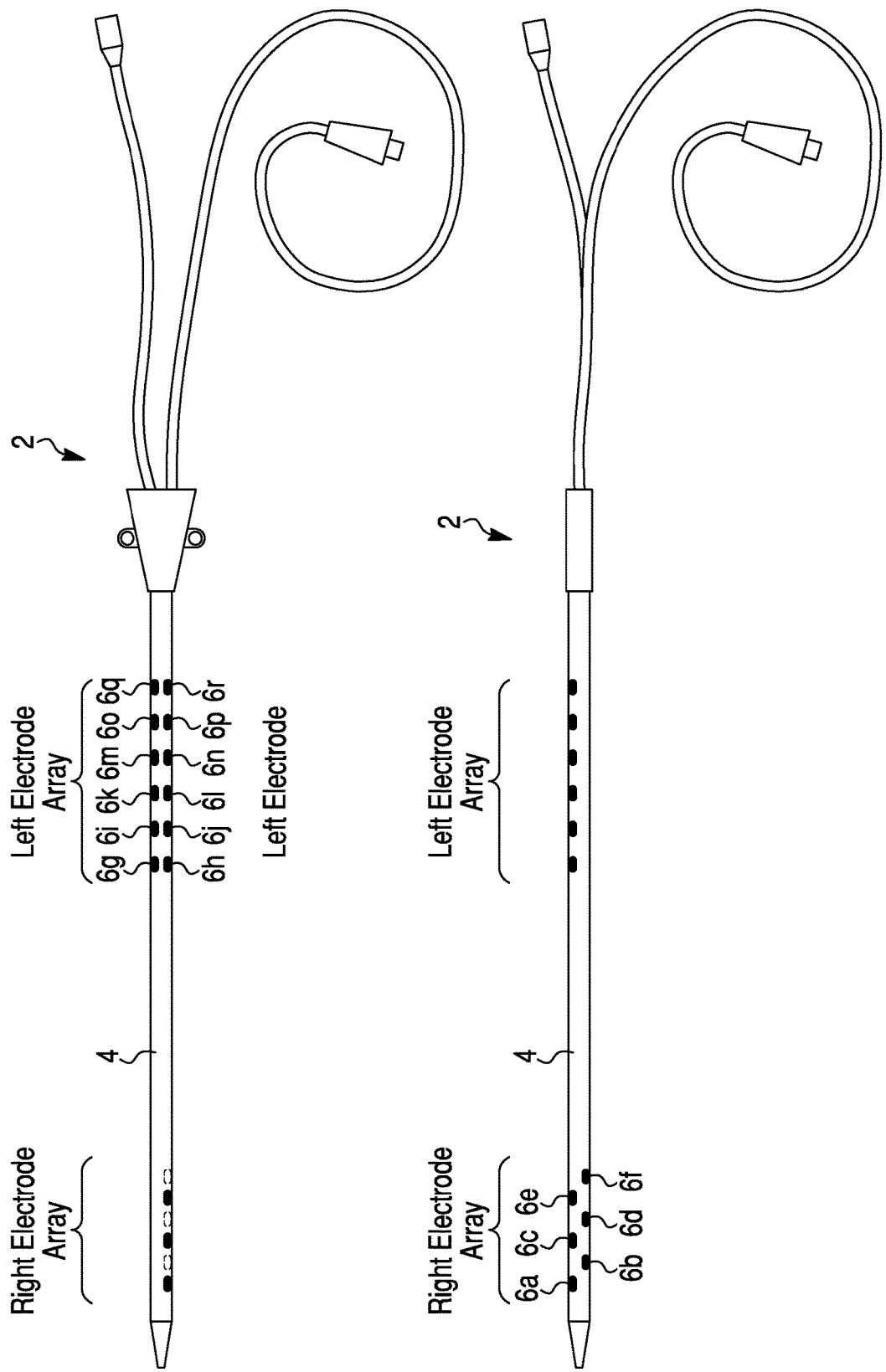

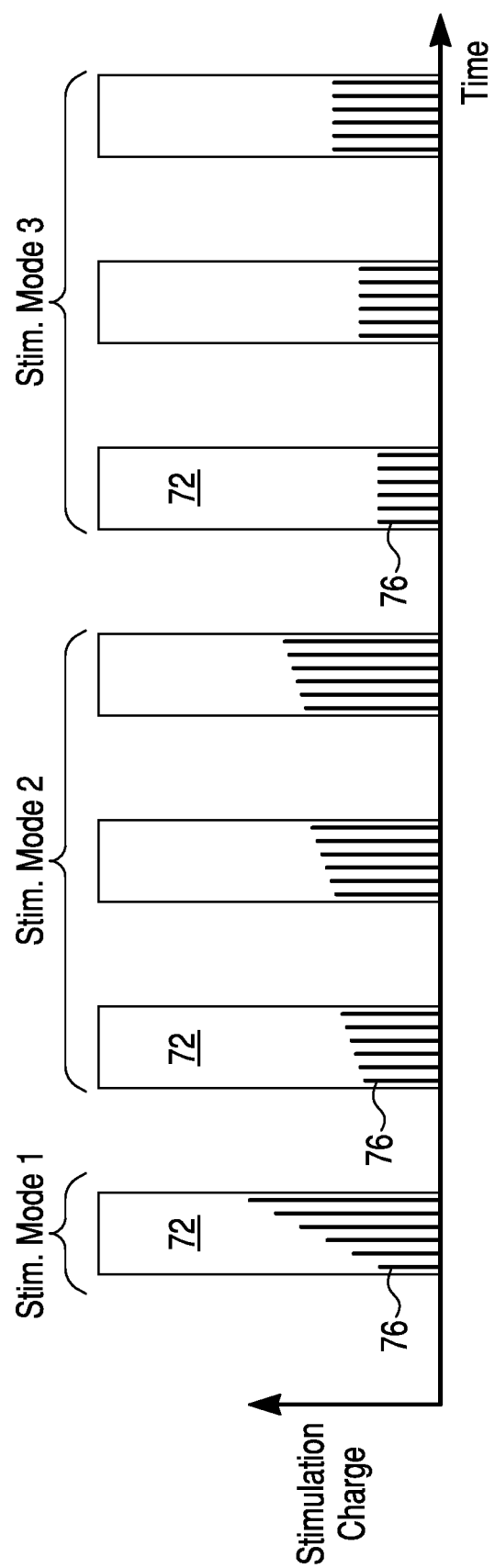

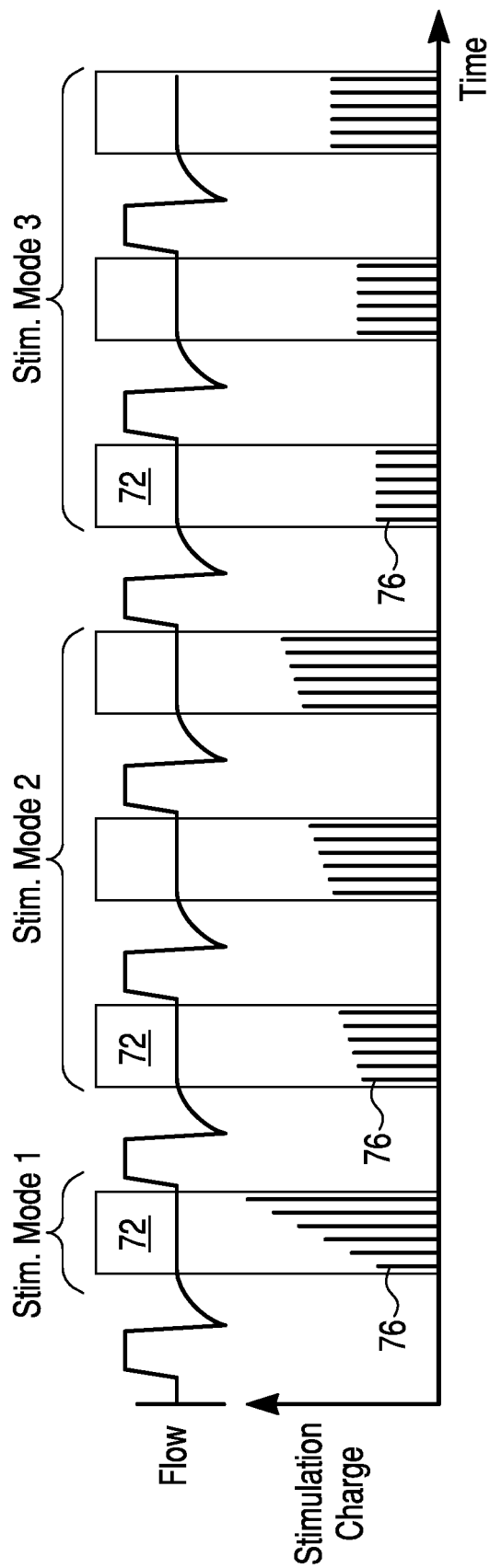

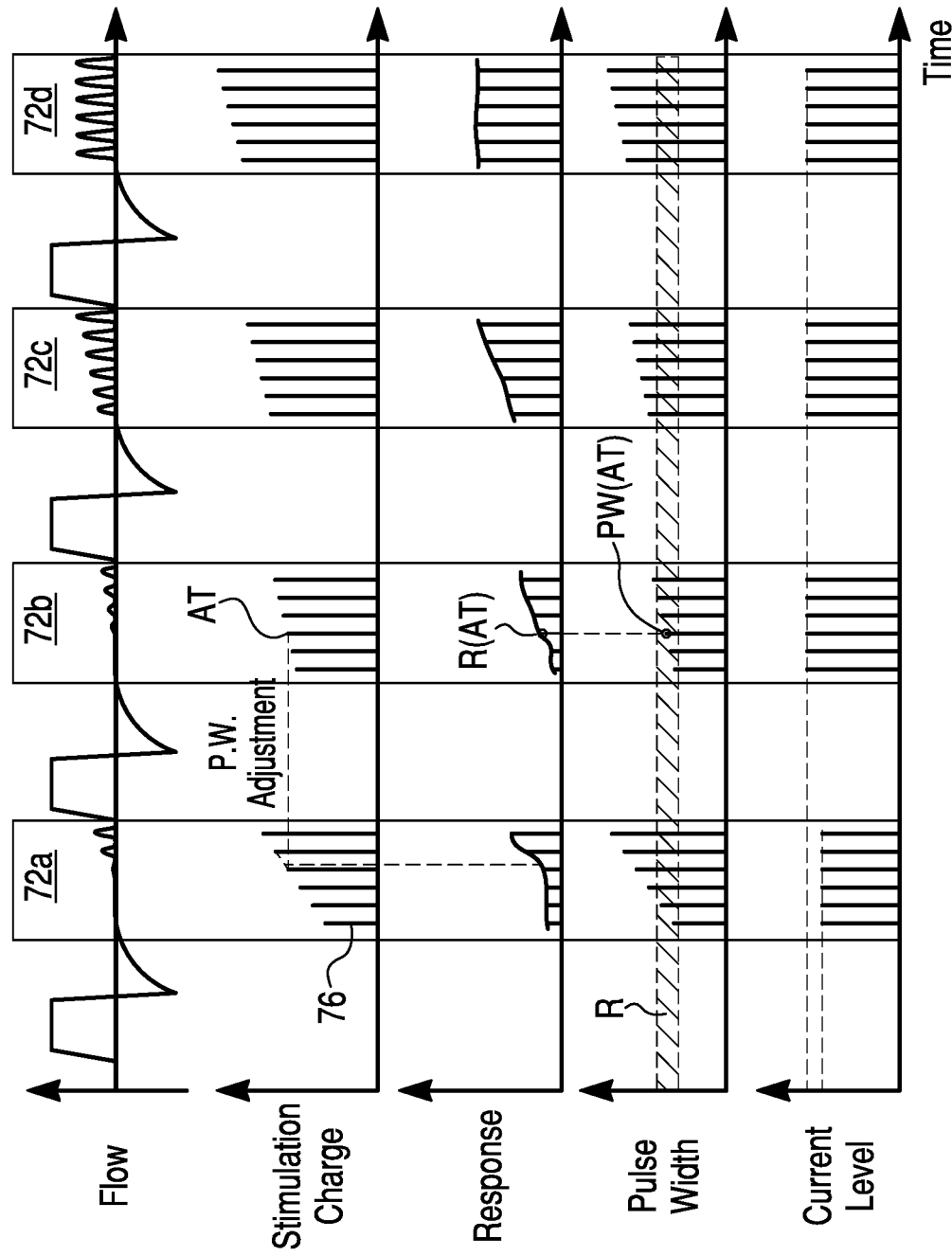

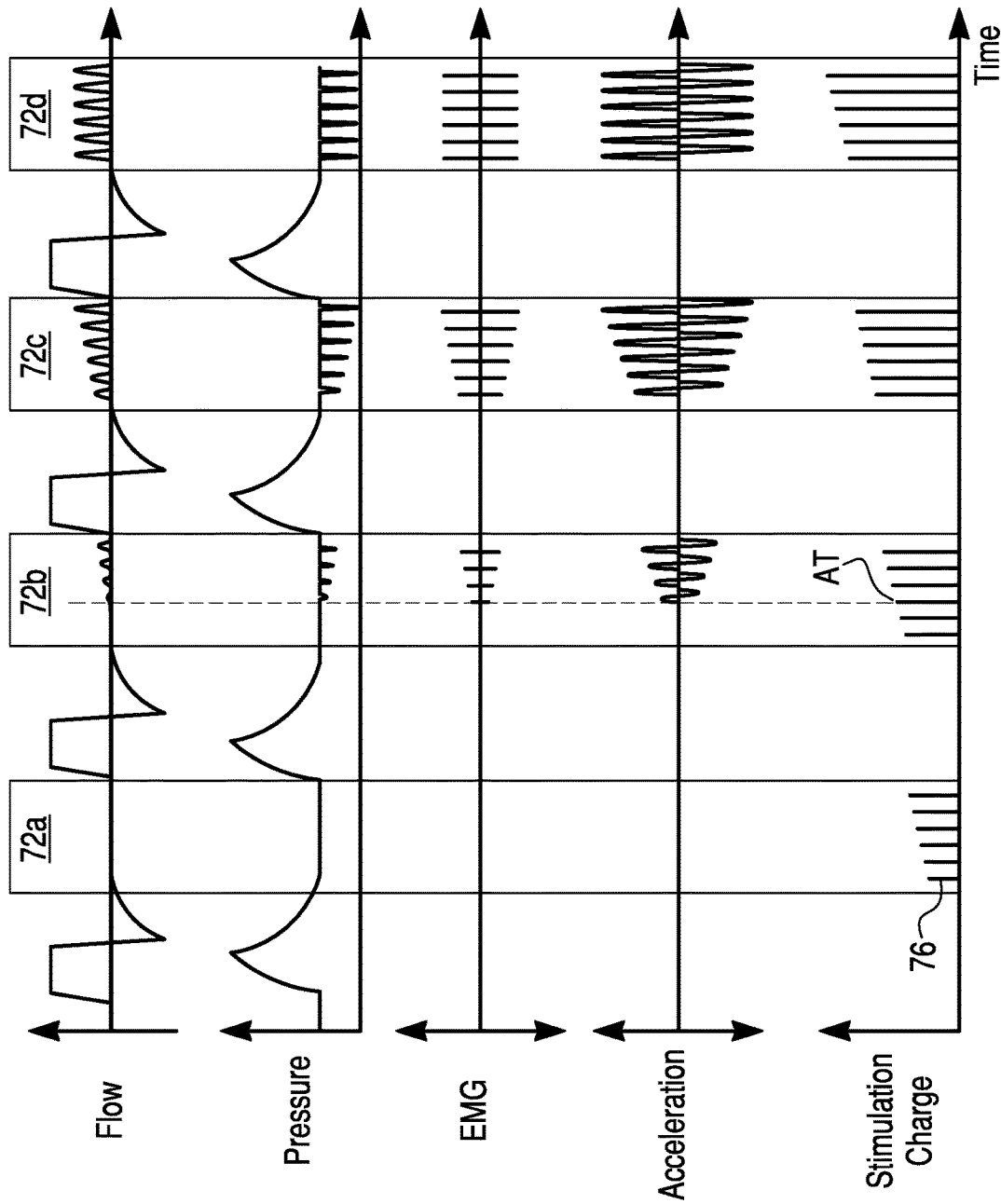

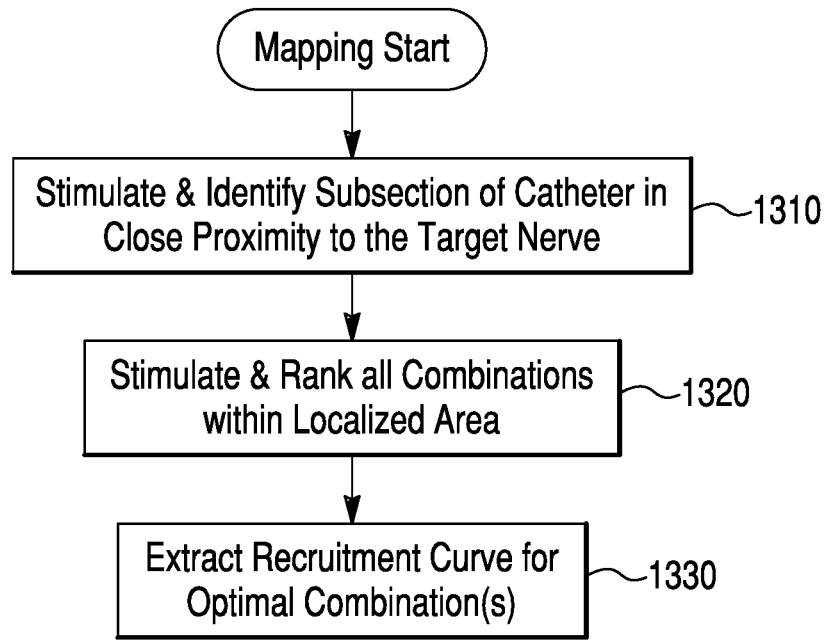

SYSTEMS AND RELATED METHODS FOR OPTIMIZATION OF MULTI-ELECTRODE NERVE PACING

CROSS-REFERENCE TO RELATED APPLICATIONS

This application is a continuation of U.S. application Ser. No. 15/427,924, filed Feb. 8, 2017 (now U.S. Pat. No. 10,391,314), which a continuation of U.S. application Ser. No. 15/095,773, filed Apr. 11, 2016 (now U.S. Pat. No. 9,597,509), which is a continuation of U.S. application Ser. No. 14/600,763, filed Jan. 20, 2015 (now U.S. Pat. No. 9,333,363, issued on May 10, 2016), which claims priority under 35 U.S.C. § 119(e) to U.S. Provisional Application No. 61/929,901, filed Jan. 21, 2014. Each of the above-referenced applications is hereby incorporated by reference herein in its entirety.

TECHNICAL FIELD

This disclosure relates to restoration, enhancement, and/or modulation of diminished neurophysiological functions using electrical stimulation. Some embodiments provide methods for mapping and selecting the optimal electrodes that are in close anatomical proximity to a target nerve. Non-limiting embodiments include nerve stimulation apparatus, electrode structures, electrodes, sensors, and related methods.

BACKGROUND

Electrical stimulation of nerves is widely applied in the treatment of a range of conditions and may be applied to control muscle activity or to generate sensations. Nerves may be stimulated by surgically implanting electrodes in, around or near the nerves and activating the electrodes by means of an implanted or external source of electricity.

The phrenic nerves normally transmit signals from the brain that cause the contractions of the diaphragm necessary for breathing. However, various conditions can prevent appropriate signals from being delivered to the phrenic nerves. These include:
  permanent or temporary injury or disease affecting the spinal cord or brain stem;
  Amyotrophic Lateral Sclerosis (ALS);
  decreased day or night ventilatory drive (e.g. central sleep apnea, Ondine's curse); and
  decreased ventilatory drive while under the influence of anesthetic agents and/or mechanical ventilation.
These conditions affect a significant number of people.

Intubation and positive pressure mechanical ventilation (MV) may be used for periods of several hours or several days, sometimes weeks, to help critically ill patients breathe while in intensive care units (ICU). Some patients may be unable to regain voluntary breathing and thus require prolonged or permanent mechanical ventilation. Although mechanical ventilation can be initially lifesaving, it has a range of significant problems and/or side effects. Mechanical ventilation:
  often causes ventilator-induced lung injury (VILI) and alveolar damage which can lead to accumulation of fluid in the lungs and increased susceptibility to infection (ventilator-associated pneumonia; VAP);
  commonly requires sedation to reduce discomfort and anxiety in acutely intubated patients;
  causes rapid atrophy of the disused diaphragm muscle (ventilator-induced diaphragm dysfunction, VIDD);
  can adversely affect venous return because the lungs are pressurized and the diaphragm is inactive;
  interferes with eating and speaking;
  requires apparatus that is not readily portable; and
  increases the risk of dying in a hospital if the patient fails to regain normal breathing and becomes ventilator-dependent.

A patient who is sedated and connected to a mechanical ventilator cannot breathe normally because the central neural drive to the diaphragm and accessory respiratory muscles is suppressed. Inactivity leads to muscle disuse atrophy and an overall decline in well-being. Diaphragm muscle atrophy occurs rapidly and can be a serious problem to the patient. According to a published study of organ donor patients (Levine et al., New England Journal of Medicine, 358: 1327-1335, 2008), after only 18 to 69 hours of mechanical ventilation, all diaphragm muscle fibers had shrunk on average by 52-57%. Muscle fiber atrophy results in muscle weakness and increased fatigability. Therefore, ventilator-induced diaphragm atrophy could cause a patient to become ventilator-dependent. It has been reported that over 840,000 ICU patients in the United States, Europe and Canada become ventilator dependent every year.

It is well known that for certain patients who have permanent respiratory insufficiency due to absent or reduced central drive descending from the brain stem, it is feasible and advantageous to rhythmically activate the diaphragm muscle by electrically stimulating ("pacing") the phrenic nerves using implanted electrodes. Several methods have been disclosed.

Method 1 uses cuff-like electrodes surgically implanted in the neck or upper chest to directly stimulate the phrenic nerves, such as the Mark IV Breathing Pacemaker System available from Avery Biomedical Devices, Inc. of Commack, N.Y., USA. The electrodes are connected to surgically implanted receivers and mated to external transmitters by antennas worn over the implanted receivers. Implanting electrodes for phrenic nerve pacing requires significant surgery that can be risky and complicated by the fact that phrenic nerves are thin (approximately 2 mm in diameter), delicate, and located amidst major blood vessels deep in the chest. This type of surgery involves significant cost and is typically only indicated for certain patients who would otherwise depend on mechanical ventilation for the rest of their lives.

Method 2 uses implanted intramuscular electrodes to pace the diaphragm, such as the NeuRx Diaphragm Pacing System® marketed by Synapse Biomedical Inc. of Oberlin, Ohio. Surgical anesthesia and laparoscopic surgery are required to map the motor points in the diaphragm muscle and suture several electrodes near the motor points. This type of surgery also involves significant time and cost and is currently only indicated for spinal cord injury (SCI) or amyotrophic lateral sclerosis (ALS) patients, who would otherwise depend on mechanical ventilation for the rest of their lives.

In some patients who were paced with either Method 1 or Method 2, it was found that the rhythmic negative-pressure breathing action provided by phrenic nerve pacing contributed to reducing the rate and extent of lung injury and infections, compared to mechanically ventilated patients. Phrenic pacing was also shown by Ayas et al. (1999; "Prevention of human diaphragm atrophy with short periods of electrical stimulation") to be an effective method for preserving or increasing the strength and the endurance of the diaphragm muscle paralyzed by a SCI. This type of evidence relates to a well-known fundamental physiological effect of electrical activation of muscle nerves, upon which the current disclosure is, in part, based on.

Method 3 relates to a system and method using intravascularly implanted electrodes to stimulate a nerve, developed by Joaquin Andres Hoffer and described in U.S. Pat. No. 8,571,662 entitled "Transvascular Nerve Stimulation Apparatus and Methods," which is hereby incorporated by reference in its entirety. Critically ill ICU patients are not typically eligible for Methods 1 and 2. For short-term use in ICU patients, Method 3 has unique advantages due to the fact that it does not require invasive surgery that would typically be performed under full anaesthesia. Method 3 rhythmically activates the diaphragm through a temporary, removable, multi-lumen, multi-electrode catheter that is percutaneously inserted into central veins (e.g., left subclavian vein, superior vena cava) of a patient. In critically ill patients who would typically fail to wean and become ventilator-dependent, the pacing therapy described in U.S. Pat. No. 8,571,662 is expected to prevent, mitigate, or reverse diaphragm muscle-disuse atrophy and maintain diaphragmatic endurance, thus facilitating successful weaning of patients from mechanical ventilation.

SUMMARY

Short-term pacing of the diaphragm muscle in ICU patients who are temporarily dependent on mechanical ventilation can be reasonably expected to prevent, slow down, or reverse the rapid progression of the typical MV-induced diaphragm muscle disuse atrophy. When the catheter is suitably placed inside the central veins as described above in connection with Method 3, it is important to select the optimum bipolar electrode combinations, which may be pairs of bipolar electrodes, for nerve stimulation. One factor for determining whether an electrode combination is optimum may be proximity to the target nerve. In selecting the optimum electrode combination, lower and safer electrical charge and currents can be used to activate the phrenic nerves, thus preventing overstimulation or unwanted activation of nearby structures such as other nerves, muscles, or the heart.

One embodiment of the present disclosure provides an automated algorithm and method to map and select optimum electrode pairs depending on pacing parameters, sensing parameters, and/or a multitude of other parameters. The algorithm and the method to map and select the optimum electrodes described in this disclosure may be useful for trans-vascular phrenic nerve pacing therapy. In addition, the paced diaphragm may restore negative pressure ventilation, thereby providing a more physiological respiratory pattern and reducing the levels of positive pressure ventilation and its harmful effects on the lungs.

Other embodiments of the disclosure include: an algorithm to generate a map of pacing parameters, sensing parameters and/or a multitude of other parameters for individual electrodes on a multi-electrode catheter, an algorithm for mapping the target nerve relative to the location of an electrode structure within a blood vessel, an algorithm for the automatic selection of optimum electrodes, and an algorithm to monitor the efficacy of the stimulation during delivery of therapy via the selected electrodes. Such algorithms may be applied in methods or embodied in apparatus. While these and other embodiments may be applied together, individual embodiments may be applied in other combinations and contexts. For example, algorithms described herein may be applied in combination with various neurovascular pacing or sensing systems known in the art for various diagnostic and/or therapeutic applications.

Embodiments of the disclosure may be applied for restoring breathing, treating conditions such as disuse muscle atrophy and chronic pain, and other uses involving nerve stimulation. Embodiments of the disclosure may be applied in the treatment of acute or chronic conditions. Embodiments of the disclosure also may be applied to evaluate the need to reposition or remove and replace electrode structures in a patient.

One embodiment of the disclosure relates to transvascular stimulation of nerves. In transvascular stimulation, suitable arrangements of one or more electrodes are positioned in a blood vessel that is anatomically close to a nerve to be stimulated. Electrical currents pass from the electrodes through a wall of the blood vessel to stimulate the target nerve.

Another embodiment of the disclosure relates to transvascular stimulation of nerves in the neck and chest of a human or other mammal (e.g., a pig, a chimpanzee). FIGS. 1 and 15 illustrate the anatomy of selected nerves and blood vessels in the neck and chest of a human and, in particular, the relative locations of the left and right phrenic nerves (PhN), vagus nerves (VN), internal jugular veins (UV), brachiocephalic veins (BCV), superior vena cava (SVC) and subclavian veins (ScV).

In one exemplary embodiment, a method of electrical stimulation may include: delivering a series of first electrical stimulations to a nerve via each of a first plurality of electrode combinations one at a time; monitoring a first patient response to each of the first electrical stimulations of the nerve; selecting a first subset of the first plurality of electrode combinations based on the first patient responses indicating that the first subset is in proximity to the nerve; based on electrodes within the first subset of the first electrode combinations, determining a second plurality of electrode combinations; delivering a series of second electrical stimulations to the nerve via each of the second plurality of electrode combinations one at a time; monitoring a second patient response to each of the second electrical stimulations of the nerve; and based on the second patient responses, selecting a second subset of the second plurality of electrode combinations, wherein the second subset includes electrode combinations having greater second patient responses than other of the second plurality of electrode combinations.

The method of electrical stimulation may additionally or alternatively include one or more of the following steps or features: the first electrical stimulations may include a plurality of electrical pulses delivered during end-expiration phases of one or more patient breaths; each of the plurality of electrical pulses may have a different charge than other of the plurality of electrical pulses; each of the plurality of electrical pulses may have the same charge as other of the plurality of electrical pulses; the second electrical stimulations may be delivered after the first electrical stimulations; each of the steps of monitoring a first patient response and monitoring a second patient response may include obtaining information from a sensor indicative of at least one of air flow, volume, or pressure; at least one of the steps of monitoring a first patient response and monitoring a second patient response may include obtaining information from a sensor indicative of at least one of electromyographic activity, central venous pressure, heart rate, chest wall acceleration, blood oxygen saturation, carbon dioxide concentration, catheter location, mechanical movement, or resistance; the first subset of the first plurality of electrode combinations may be located along a portion of a catheter; the electrode combinations of the first and second plurality of electrode combinations may include bipolar electrode pairs; selecting the first subset of the first plurality of electrode combinations may include ranking the electrode combinations of the first plurality of electrode combinations with respect to the first patient responses, and selecting the second subset of the second plurality of electrode combinations may include ranking the electrode combinations of the second plurality of electrode combinations with respect to the second patient responses, and the first and second patient responses may be indicative of diaphragm responses to the respective first and second electrical stimulations; at least one of the steps of selecting the first subset of the first plurality of electrode combinations or selecting the second subset of the second plurality of electrode combinations may include ranking electrode combinations with respect to activation threshold and discarding electrode combinations having activation thresholds higher than activation thresholds of other electrode combinations; at least one of the first or second patient responses may include an undesirable effect on a physiological feature other than the diaphragm, and selection of the respective first or second subset of the first or second plurality of electrode combinations does not include an electrode combination causing the undesirable effect; the method may further comprise determining a recruitment curve corresponding to at least one electrode combination of the second subset of the second plurality of electrode combinations; the method may further comprise adjusting a pulse width and an amplitude of the current to one of the electrode combinations of the first or second plurality of electrode combinations, such that the first or second electrical stimulations cause graded nerve recruitment within a preset pulse width range; the electrodes within the first plurality of electrode combinations may be located on an elongated body; the electrodes within the first plurality of electrode combinations may be proximal electrodes located on a proximal portion of the elongated body, the nerve may be a left phrenic nerve, and the elongated body may further include distal electrodes located on a distal portion of the elongated body, and the method may further include: delivering a series of third electrical stimulations to a right phrenic nerve via each of a third plurality of electrode combinations one at a time, wherein the third plurality of electrode combinations includes the distal electrodes; monitoring a third patient response to each of the third electrical stimulations of the nerve; selecting a third subset of the third plurality of electrode combinations based on the third patient responses indicating that the third subset is in proximity to the right phrenic nerve; based on electrodes within the third subset of the third electrode combinations, determining a fourth plurality of electrode combinations; delivering a series of fourth electrical stimulations to the right phrenic nerve via each of the fourth plurality of electrode combinations one at a time; monitoring a fourth patient response to each of the fourth electrical stimulations of the nerve; and based on the fourth patient responses, selecting a fourth subset of the fourth plurality of electrode combinations, wherein the fourth subset includes electrode combinations having greater fourth patient responses than other of the fourth plurality of electrode combinations; the method may further include positioning the proximal portion of the elongated body in a first blood vessel proximate a left phrenic nerve and positioning the distal portion of the elongated body in a second blood vessel proximate a right phrenic nerve; and a rate of the first electrical stimulations and a rate of the second electrical stimulations may be based at least in part on: a) a duration of a corresponding end-expiratory phase, and b) a duration of the corresponding first and second patient responses.

In another exemplary embodiment, a method of electrical stimulation may include: delivering a first electrical stimulation to a nerve using a first electrode combination, wherein the first electrical stimulation includes a first plurality of electrical pulses delivered during an end-expiration phase of each of one or more first patient breaths; delivering a second electrical stimulation to the nerve using a second electrode combination, wherein the second electrical stimulation includes a second plurality of electrical pulses delivered during an end-expiration phase of each of one or more second patient breaths different than the first patient breaths; monitoring a response of a diaphragm to each of the first and second electrical stimulations; and based on the diaphragm responses, determining a nerve activation threshold corresponding to each of the first and second electrode combinations.

The method of electrical stimulation may additionally or alternatively include one or more of the following steps or features: the first and second electrode combinations may be located in a blood vessel of a patient receiving breathing assistance from a ventilator; the nerve may be a phrenic nerve; the first and second electrode combinations may include bipolar electrode pairs; monitoring the response of the diaphragm may include sensing with a sensor at least one of flow, volume, or pressure; the nerve activation threshold may be a threshold charge value between a first charge value that will not cause nerve recruitment and a second charge value that will always cause nerve recruitment; approximately half of a plurality of electrical pulses, each delivering a nominal threshold charge value, may cause nerve recruitment.

In one embodiment, a diaphragm pacing system may include: an electrode assembly including a plurality of electrodes; at least one sensor configured to monitor a patient response to electrical stimulation; and a stimulation control unit configured to: deliver a series of first electrical stimulations to a nerve via each of a first plurality of electrode combinations one at a time; receive input from the at least one sensor indicative of first patient responses to the series of first electrical stimulations; select a first subset of the first plurality of electrode combinations based on the first patient responses indicating that the first subset is in proximity to the nerve; based on electrodes within the first subset of the first electrode combinations, determine a second plurality of electrode combinations; deliver a series of second electrical stimulations to the nerve via each of the second plurality of electrode combinations one at a time; receive input from the at least one sensor indicative of second patient responses to the series of second electrical stimulations; and based on the second patient responses, select a second subset of the second plurality of electrode combinations, wherein the second subset includes electrode combinations having greater second patient responses than other of the second plurality of electrode combinations.

The system may additionally or alternatively include one or more of the following features: the electrode assembly may be a catheter configured for insertion into a venous system of a patient; the patient response may be at least one of air flow, volume, or pressure; the patient response may be at least one of electromyographic activity, central venous pressure, heart rate, chest wall acceleration, blood oxygen saturation, carbon dioxide concentration, catheter location, mechanical movement, or resistance; each of the first and second electrical stimulations may include a plurality of electrical pulses, and the stimulation control unit may be further configured to deliver the pluralities of electrical pulses during end-expiratory phases of a patient receiving breathing assistance from a ventilator; the patient responses may be indicative of a diaphragm response to electrical stimulation; the stimulation control unit may be configured to select the second subset such that the second subset includes electrode combinations having lower activation thresholds than other of the second plurality of electrode combinations; the stimulation control unit may be configured to halt delivery of electrical stimulations to an electrode combination of the first or second plurality of electrode combinations based on a determination that an activation threshold corresponding to the electrode combination is higher than an activation threshold corresponding to another electrode combination of the first or second plurality of electrode combinations; the stimulation control unit may configured to adjust a pulse width and an amplitude of the current of one of the first or second electrical stimulations; the stimulation control unit may be configured to adjust an amplitude of the current of one of the first or second electrical stimulations if the patient response to the one of the first or second electrical stimulations indicates supra-maximal recruitment of a nerve; and the at least one sensor may include two or more sensors.

Further embodiments of the disclosure and features of example embodiments are illustrated in the appended drawings and/or described in the text of this specification and/or described in the accompanying claims. It may be understood that both the foregoing general description and the following detailed description are exemplary and explanatory only and are not restrictive of the invention, as claimed.

BRIEF DESCRIPTION OF THE DRAWINGS

FIG. 3 is one example of multi-electrode catheter that can be used for trans-vascular phrenic nerve stimulation to be positioned within the left subclavian vein and superior vena cava of the patient, according to an exemplary embodiment.

FIG. 7 shows different stimulation modes that can be used for stimulating phrenic nerves, according to an exemplary embodiment.

FIG. 8 shows different stimulation modes that can be used in synchrony with mechanical ventilation, with stimulation delivered during the end-expiration phases.

FIG. 9A illustrates characteristics of diaphragm pacing in synchrony with mechanical ventilation, according to an exemplary embodiment. The plot shows flow signals, stimulation charge, diaphragm response, pulse width modulation, and current. It also shows an exemplary preconfigured Pulse Width Zone indicating the range of pulse width values within which threshold activation is desired.

FIG. 9B illustrates diaphragm pacing in synchrony with mechanical ventilation and shows flow, pressure, EMG, and acceleration measurements corresponding to electrical stimulation of a phrenic nerve, according to an exemplary embodiment.

FIG. 13 shows a flowchart of a mapping algorithm, according to an exemplary embodiment.

DETAILED DESCRIPTION

General Overview

This disclosure describes, among other embodiments, systems and related methods for selecting electrode combinations to be used during nerve pacing procedures. Multiple electrode combinations of an electrode assembly of a nerve pacing system, such as a diaphragm pacing system, may be mapped (or tested) to determine each combination's relative efficacy when electrically stimulating a target nerve. Stimulation efficacy in this context may refer to, for example, the ability to consistently stimulate a nerve with lowest possible charge per stimulation pulse. Typically, the charge required to elicit stimulation depends on the electrode location relative to a target nerve—the shorter the distance between the electrode combination and target, the lower the required charge per pulse. At various stages of the mapping process, electrode combinations that require higher charges to stimulate a nerve, that do not maximally stimulate the nerve fast enough when modulating charge, that maximally stimulate the nerve too soon when modulating charge, that do not stimulate the nerve in a stable and predictable manner, that cause undesired stimulation of other nerves or anatomy, or that otherwise are non-optimal may be discarded as candidates for use in a nerve pacing procedure. In one embodiment, the mapping process may be carried out prior to diaphragm pacing via electrical stimulation of the phrenic nerves, and the selected electrode combination or combinations may be used to stimulate the phrenic nerves during subsequent diaphragm pacing. In some embodiments, the mapping process may be carried out after the start of diaphragm pacing to ensure that the optimal electrode combinations are being used to stimulate the phrenic nerves. In other embodiments, the mapping process may be carried out both prior to diaphragm pacing and at one or more times during pacing to ensure that the optimal electrodes are used during the entire stimulation period.

Figure 1:
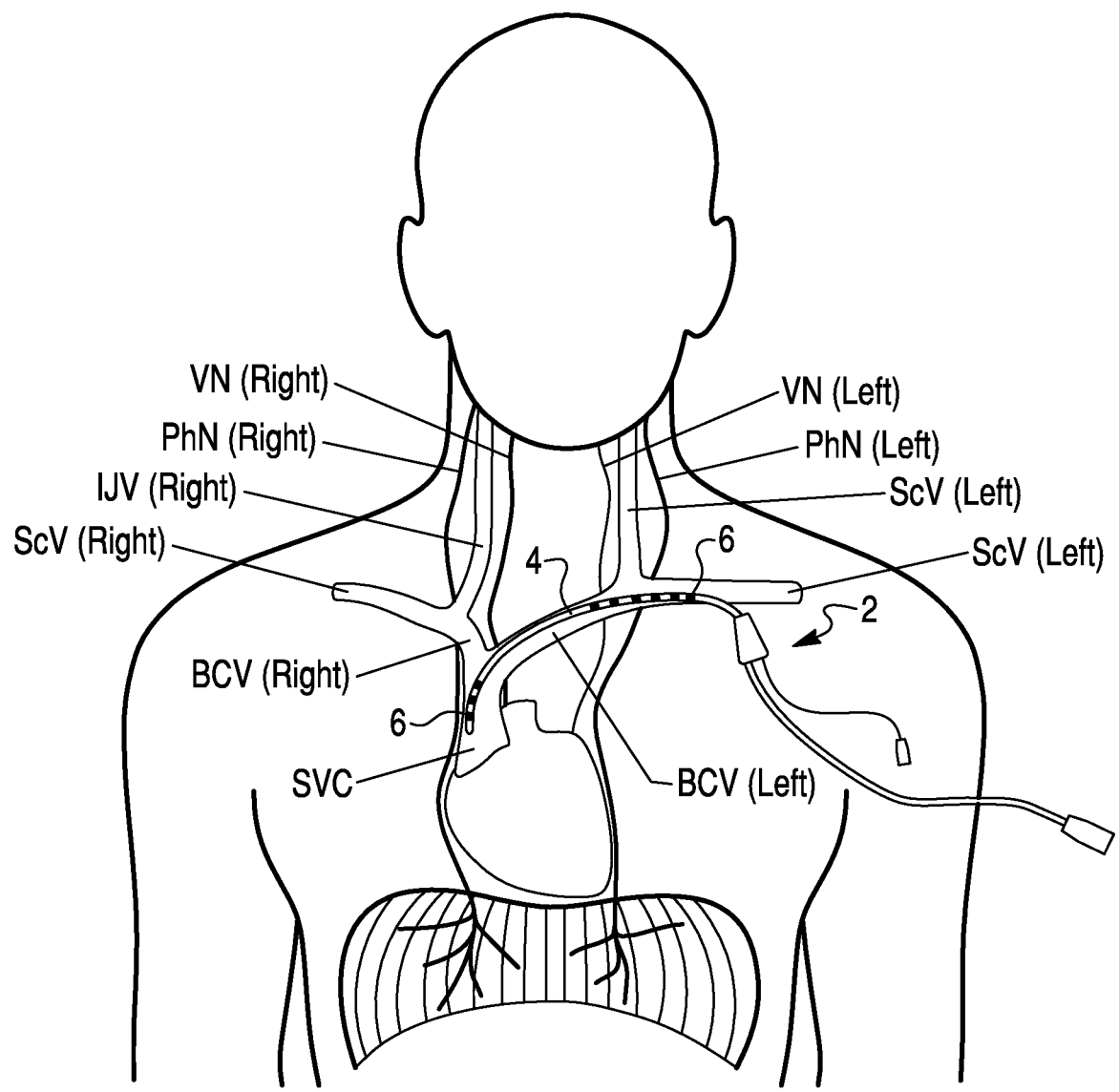
FIG. 1 is a schematic diagram showing the locations of the left and right phrenic nerves in a patient in relation to the heart and diaphragm of the patient and the placement of a multi-electrode catheter, according to an exemplary embodiment.

The components of an example diaphragm pacing system will now be described in detail. As shown in FIG. 1, the system may include a multi-electrode assembly 2. The assembly 2 may include an elongated body 4, in this example a catheter, where electrodes 6 are placed longitudinally along the length of the elongated body 4. The catheter may be percutaneously inserted rapidly using the Seldinger technique with assistance from ultrasound imaging or any other suitable insertion method. A guide wire may be first inserted through a hypodermic needle into the vein, and the distal tip of the catheter may then be passed over the guide wire and advanced into the vein. The shape and mechanical properties of the catheter may be designed to urge the catheter to gently hug the vein wall in regions adjacent to the right and left phrenic nerves.

FIG. 3 illustrates one embodiment of a multi-electrode assembly 2. FIG. 3 shows two views of assembly 2 rotated 90 degrees relative to each other about the axis of elongated body 4. The elongated body 4 may be a catheter having a plurality of distal electrodes 6a-6f and a plurality of proximal electrodes 6g-6r. Although six distal electrodes and twelve proximal electrodes are shown, the elongated body 4 may include any number of electrodes. The electrodes may be held on a plurality of electrode assemblies within the catheter. In one embodiment, the electrodes may be exposed to the exterior of the elongated body 4 through apertures. The apertures may confine electrical fields created by electrode combinations to specific desired areas. The elongated body 4 may be configured such that the left electrode array (electrodes 6g-6r) is configured to stimulate a patient's left phrenic nerve and the right electrode array (6a-6f) is configured to stimulate a patient's right phrenic nerve.

Figure 4A:
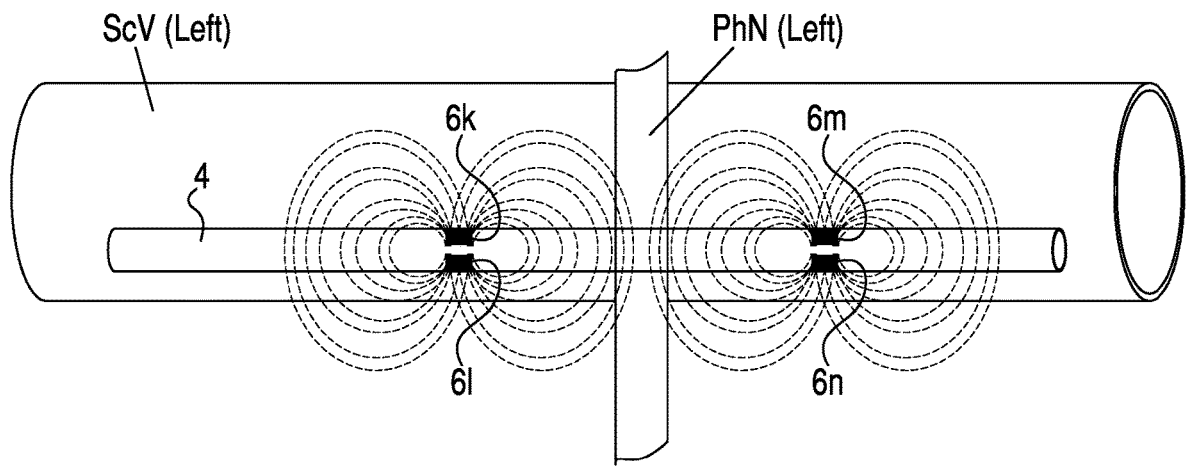
FIG. 4A is one example of two pairs of catheter-mounted phrenic nerve stimulating electrodes positioned within the left subclavian vein of the patient in close proximity to the left phrenic nerve, according to an exemplary embodiment.
Figure 4B:
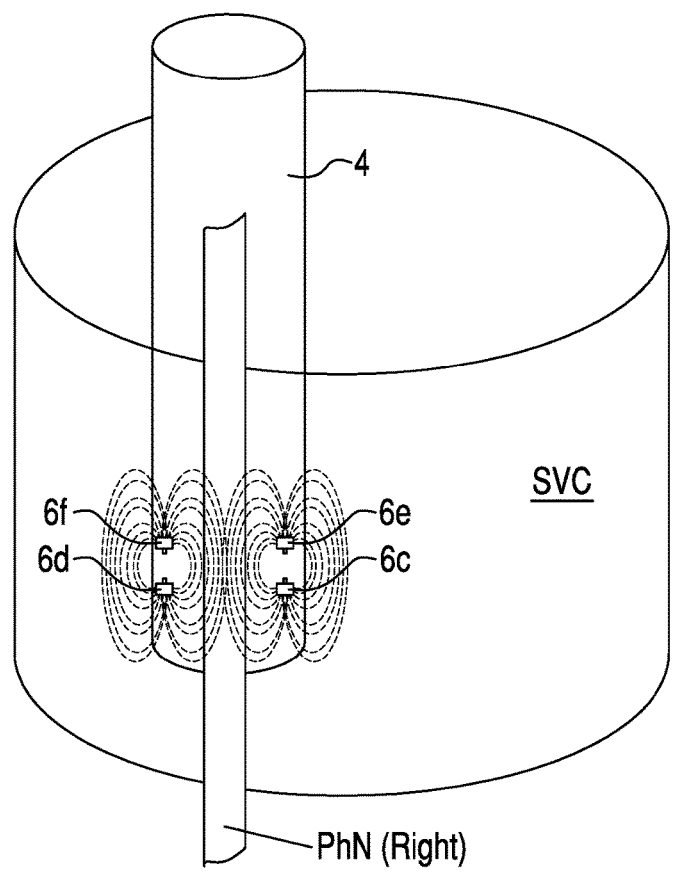
FIG. 4B is one example of two pairs of catheter-mounted phrenic nerve stimulating electrodes positioned within the superior vena cava of the patient in close proximity to the right phrenic nerve, according to an exemplary embodiment.

While two electrodes may be used for bipolar stimulation of each of the left and right phrenic nerves, it will be appreciated that other numbers of electrodes may be practiced with embodiments of the present disclosure and may form an electrode combination. For example, four electrodes can be used for stimulating each phrenic nerve, as shown in FIGS. 4A and 4B. In some embodiments, a single electrode may be used for so-called monopolar stimulation of nerves, in which case the stimulation circuit is completed by using a reference electrode placed at another location in or on the body. An electrode combination may be any set of one or more electrodes configured to electrically stimulate a nerve. Charge-balanced biphasic stimulation pulses may minimize tissue damage and electrode corrosion.

FIGS. 4A and FIG. 4B illustrate one embodiment of an elongated body 4, which may be a catheter or other structure to support electrodes, showing two channels of transvascular stimulation delivered to the left phrenic nerve PhN (Left) by endovascular electrodes placed in the left subclavian vein and two channels of transvascular stimulation delivered to the right phrenic nerve PhN (Right) by endovascular electrodes placed along the lateral wall of the superior vena cava SVC. Each phrenic nerve can be partially or fully recruited from more than one endovascular electrode combination.

Partial nerve recruitment from more than one electrode combination may be useful to reduce muscle fatigue over time. The diaphragm pacing system may alternate back and forth between electrode combinations (e.g., between the left pair and the right pair in FIG. 4A; or between the left pair and the right pair in FIG. 4B) used for nerve stimulation based on a certain time interval or a certain number of breaths. In another embodiment that may reduce muscle fatigue, a nerve may be recruited using two electrode combinations that are stimulated out of phase, thus allowing stimulation of each channel at a lower rate without causing increased ripple in the resulting muscle force. Use of multiple electrode combinations may also allow for consistent recruitment of a nerve if the elongated body 4 moves within the patient.

For more information regarding the endovascular placement of a plurality of electrodes as well as the configuration of electrode structures that can be practiced with embodiments of the present disclosure, see U.S. application Ser. No. 12/524,571, filed Jul. 25, 2009, now U.S. Pat. No. 8,571,662, U.S. Provisional Application No. 61/907,993, filed Nov. 22, 2013, titled "Apparatus for Assisted Breathing by Transvascular Nerve Stimulation and Related Methods," and U.S. application Ser. No. 14/550,485, filed Nov. 21, 2014, titled "Apparatus and Methods for Assisted Breathing by Transvascular Nerve Stimulation," the disclosures of each of which are hereby expressly incorporated by reference herein for all purposes in their entirety. Additionally, while electrodes receiving charge-balanced biphasic stimulus pulses may be utilized to emit the stimulation pulses into the phrenic nerves, other configurations are possible. For example, several cathodal electrode contacts may be used in conjunction with a single anodal electrode contact, or vice versa.

Figure 2:
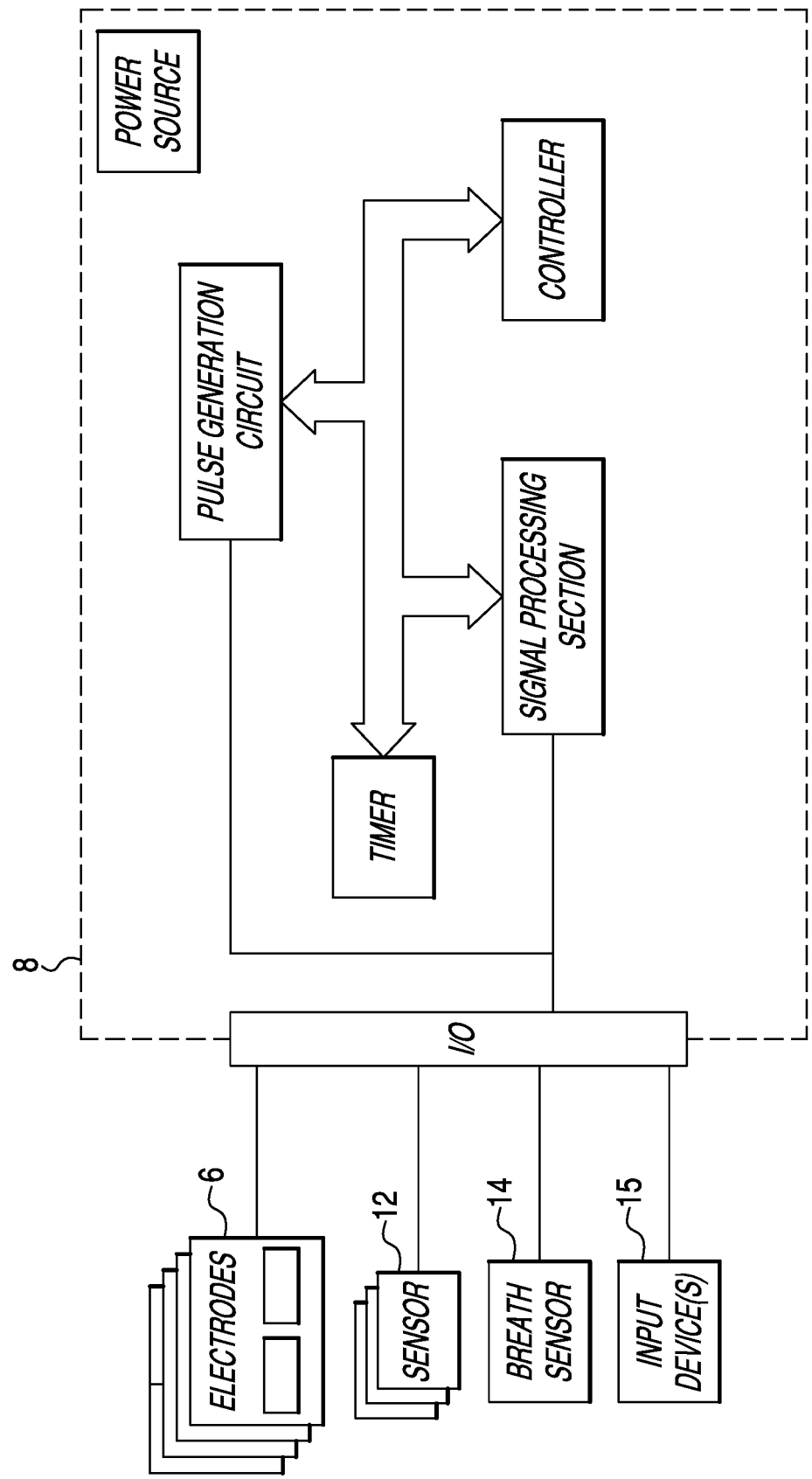
FIG. 2 is a block diagram of the components of one embodiment of a diaphragm pacing system.

Referring to FIG. 2, a diaphragm pacing system may include electrodes 6 in electrical communication with a stimulation control unit 8. Each electrode may be electrically connected to the stimulation control unit 8 via lead(s). The system may further include one or more sensors 12 configured to monitor the response to stimulation and/or other physiological characteristics of the patient. One or more sensors 12 can be part of a feedback control scheme for regulating the stimulation administered to the patient.

The one or more sensors 12 can transmit data to the stimulation control unit 8 indicative of one or more of the following: electromyographic activity (intramuscular, surface, and/or intraesophageally monitored), central venous pressure (any specific component of this signal), heart rate, chest wall acceleration, blood oxygen saturation, carbon dioxide concentration, catheter position/depth within vein, mechanical movement (e.g., from accelerometers, length gauges, and/or strain gauges) resistance (e.g., from impedance pneumographs, and/or piezoresistive sensors) and/or other physiological or mechanical parameters. It will be appreciated that the information can be appropriately processed (e.g., filtered, conditioned, amplified, etc.) prior to use by the stimulation control unit 8.

The term "volume" as used herein includes, but is not limited to, Inspired Tidal Volume, Expired Tidal Volume, or Minute Volume. The term "pressure" as used herein includes, but is not limited to, Airway Pressure, Alveolar Pressure, Ventilator Pressure, Esophageal Pressure, Gastric Pressure, Transdiaphragmatic Pressure, Intra-Thoracic Pressure, Positive End-Expiratory Pressure, or Pleural Pressure. Any pressure may be expressed via its Peak Pressure, Mean Pressure, Baseline Pressure, or Pressure-Time Product associated with a phase of a ventilator breath. The term "flow"

as used herein includes, but is not limited to, Inspiratory Air Flow or Expiratory Air Flow.

The multi-electrode assembly 2 can also optionally monitor physiological variables of the subject by virtue of its placement in the central veins. Such monitored physiological variables can include, but are not limited to: central venous pressure, electrocardiogram, and mixed venous oxygen saturation.

The diaphragm pacing system can additionally or alternatively include a breath sensor 14 (FIG. 2) for sensing parameters of the ventilator. In that regard, the breath sensor 14 can be configured to interface with any standard breathing circuit used in critical care ventilators and therefore the pacing system may be independent of the brand and model of ventilator used. The breath sensor 14, by virtue of its location in series with the breathing circuit, may monitor and/or measure several ventilation parameters and communicate such parameters to the stimulation control unit 8. The breath sensor 14 can be part of a feedback control scheme for regulating the stimulation administered to the patient. The sensed, calculated or derived ventilation parameters may include, but are not limited to, airflow (inspired and/or expired), volume, and pressure (airway, esophageal, gastric, and/or some combination/derivative of the former). In some embodiments, other sensors may aid in the procurement of one or more ventilation parameters. In one embodiment, the breath sensor 14 may monitor flow, volume, or pressure from the breathing circuit between a patient and a ventilator. In another embodiment, the breath sensor 14 may communicate directly with the ventilator to determine flow, volume, or pressure.

The example parameters may be measured both to and from the ventilator. The breath sensor 14 may be external to the ventilator so that the system is independent of ventilator model. However, the diaphragm pacing system could also be integrated to use a ventilator's internal sensors or the signals externally supplied by the ventilator for proper operation so that an additional external breath sensor can be omitted.

The stimulation control unit 8 may function, in part, as a signal generator for providing therapy to the diaphragm in response to information received from the one or more of the sensors 12, 14 and/or information programmed into the system by the clinician. The clinician or other user may input information into the stimulation control unit 8 using one or more input devices 15. Input device 15 may include a keyboard to manually enter information or may include a ventilator or other device in communication with the stimulation control unit 8. Input information, received from a user or another device, may include any information used during or otherwise relevant to the mapping process or diaphragm pacing. The stimulation control unit 8 may be configured to deliver fully programmable stimulation.

As shown in FIG. 2, the stimulation control unit 8 of the diaphragm pacing system may further include a power source, a pulse generation circuit, a timer, a signal processing section, and a controller, each configured to execute, via hardware, software, or any other necessary components, the various functions and processes described herein. Each of the diaphragm pacing system components shown in FIG. 2 may be electrically coupled or otherwise in communication with the various other components. In one embodiment, the controller may be a distributed control system.

Once the catheter is fully inserted in the desired blood vessel(s) (FIG. 1), the process of mapping the electrodes can be initialized. Referring to FIG. 3, selective stimulation of the distal set of electrodes may be used to locate the right phrenic nerve, and selective stimulation of the proximal set of electrodes may be used to locate the left phrenic nerve.

Electrode Configuration/Orientation Relative to Nerve

In addition to proximity of electrodes to a nerve, electrode configuration relative to a nerve is a factor that may reduce the amount of electrical current required to stimulate nerve axons. In theory and in practice, nerve axons require lower activation currents when the electrodes and the direction of current flow are parallel to the nerve (such as shown in FIGS. 4A and 4B), thus producing a longitudinal transmembrane depolarization of sufficient magnitude to initiate action potentials. Since the direction a nerve courses may not be exactly known and can vary from one individual to another, various electrode combinations can be tested to ensure that the optimal electrodes are selected during nerve stimulation. The embodiment of FIG. 3 may include two parallel rows of electrodes, from among which pairs can be selected having various orientations relative to the catheter and the nerve.

Stimulation Patterns and Recruitment Curve Development During Mapping

Figure 5:
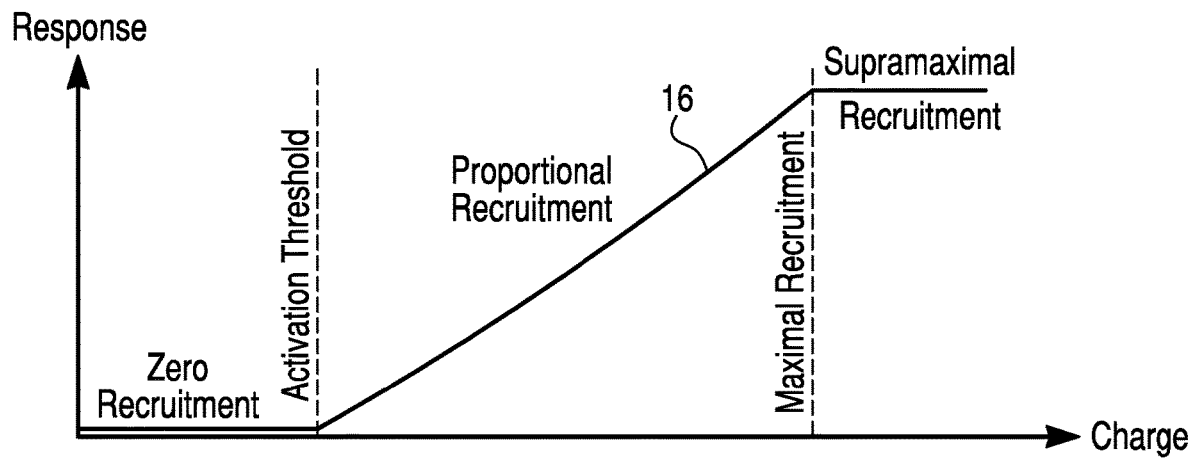
FIG. 5 shows a theoretical electrical recruitment curve for a target nerve, according to an exemplary embodiment.

Referring to FIG. 5, recruitment curves or sigmoidals may be used to characterize the response of the diaphragm to nerve stimulation. A recruitment curve may be developed by stimulating a nerve with a specific electrode combination multiple times (e.g., delivering multiple electrical pulses 76, such as those shown in FIGS. 7-9), measuring the diaphragm's response, and preparing a line of best fit to develop a model of the diaphragm's response. Thus, recruitment curves may be unique to each stimulation site and electrode combination.

FIG. 5 depicts an example of a recruitment curve 16 that may include five elements or portions. The first element of the curve is termed Zero Recruitment, and may correspond to stimulation eliciting no response from the muscle (e.g., the diaphragm). In one embodiment of the Zero Recruitment portion, two or three electrical pulses 76 (see FIG. 7) may be delivered to the nerve, which may minimize the time required and the stimulation delivered during this phase. The Zero Recruitment portion may help a user identify the Activation Threshold, which is when the muscle begins to respond to nerve stimulation. This second portion, the Activation Threshold, may represent a charge level that has a certain chance (e.g., 50%) of causing a threshold activation or contraction of the muscle. The Activation Threshold may be defined at any percentage and can be lower or higher than 50%. The third portion, Proportional Recruitment, is a part of the recruitment curve 16 that describes the relationship between charge level and recruitment between the Activation Threshold and the Maximal Recruitment level. The Proportional Recruitment section of the recruitment curve may be used to generate stimulation parameters for use during therapy. The fourth portion, Maximal Recruitment, is the charge level at which the highest possible muscle response is generated. The Maximal Recruitment point demarks the end of the Proportional Recruitment section of the recruitment curve. The last portion, termed as Supramaximal Recruitment, is any recruitment at charges larger than the Maximal Recruitment charge. The slope of this region may be less than the Proportional Recruitment region.

Figure 10A:
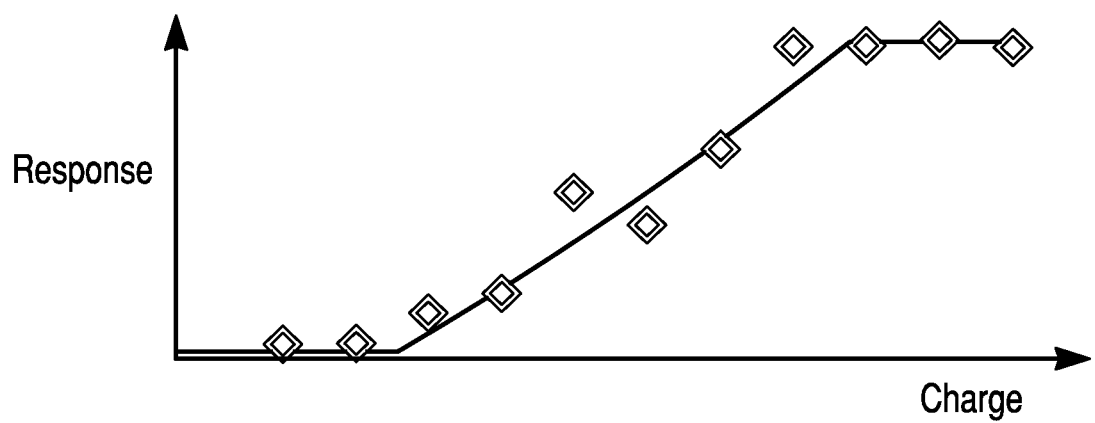
FIG. 10A is an example of recruitment curve acquired by best-fitting of a set of individual data points, according to an exemplary embodiment.
Figure 10B:
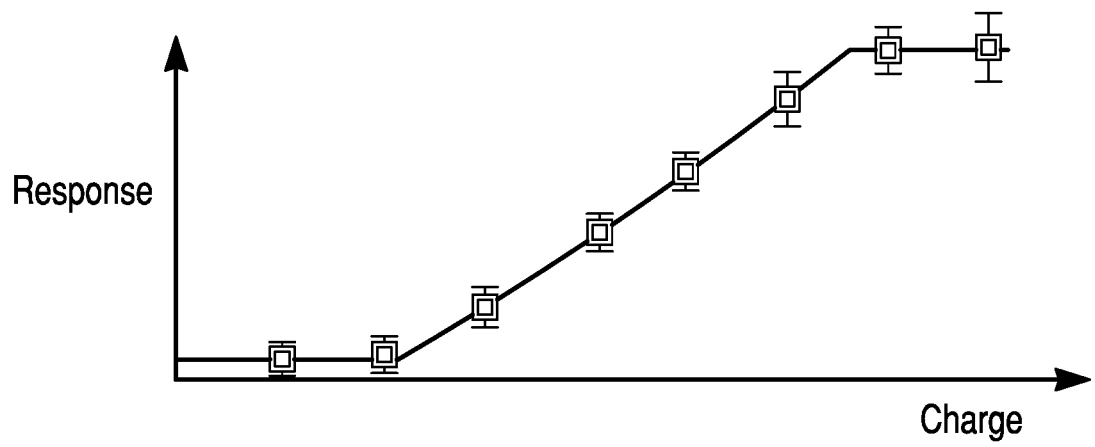
FIG. 10B is an example of recruitment curve acquired by averaging multiple data points obtained using each pulse width value, according to an exemplary embodiment.

One aspect of this disclosure involves the automated, feedback-controlled, generation of a recruitment curve as depicted in FIG. 5, FIG. 10A, and FIG. 10B. As will be described in greater detail below, the stimulation control unit 8 may deliver a ramp of stimulation pulses of increasing intensity while monitoring the response of the body, which may reduce the time required and stimulation delivered during the recruitment curve generation process. The ramp of stimulation and quantification of stimulation pulses can be achieved with a single data point per charge delivered (FIG. 10A), or multiple data points per charge delivered (FIG. 10B).

The automated generation of a recruitment curve may entail the stimulation control unit 8 delivering a ramp of stimulation (a plurality of electrical pulses 76) based on the physiological response elicited by prior pulses within the ramp of stimulation. In the event that stimulation and response parameters are not within a configurable range or threshold, the control system may halt stimulation and adjust stimulation parameters appropriately. A new ramp of stimulation may then be delivered for sigmoidal acquisition at the reconfigured charge. A complete recruitment curve may then be generated, without delivering unnecessary stimulation that would not contribute towards the generation of a satisfactory recruitment curve, as defined by the configurable thresholds. One embodiment may feature a threshold defining the appropriate pulse width range for the activation threshold; if activation is not detected within the configured pulse width zone the system may halt stimulation and increase or decrease the pulse current before commencing stimulation (see FIGS. 9 and 14C). Other embodiments may feature a threshold defining the appropriate current range for the activation threshold while keeping pulse width constant; if activation is not detected within the configured current zone, the system may halt stimulation and increase or decrease the pulse width before commencing stimulation. Other embodiments can use a combination of parameters to reconfigure charge delivered and may feature configurable zones for parameters including, but not limited to: zero recruitment, proportional recruitment, and supramaximal recruitment, as depicted in FIG. 5.

One aspect of the disclosure provides a method for mapping the best electrodes for recruiting the phrenic nerves for diaphragm pacing in synchrony with Mechanical Ventilation, without having to discontinue Mechanical Ventilation during the mapping process. The method may use a multi-electrode catheter and an automated feedback-control algorithm that intelligently selects a subsection of electrodes and may minimize the time required and stimulation delivered as part of the mapping process. As described further in connection with FIG. 13, electrode combinations may be selected for evaluation based on the physiological response (e.g., the diaphragm response) to prior stimulation. The physiological response to stimulation may be quantified by monitoring the resultant change in the airway pressure, airway flow, Electromyography, chest wall acceleration, or any other signal resulting from or correlated with contraction of the diaphragm. In the embodiment of FIG. 8, for example, stimulation may be delivered during the end-expiration (quiet) phase (see FIG. 6) of the patient's breathing cycle, and as such does not interrupt regular Mechanical Ventilation.

Figure 6:
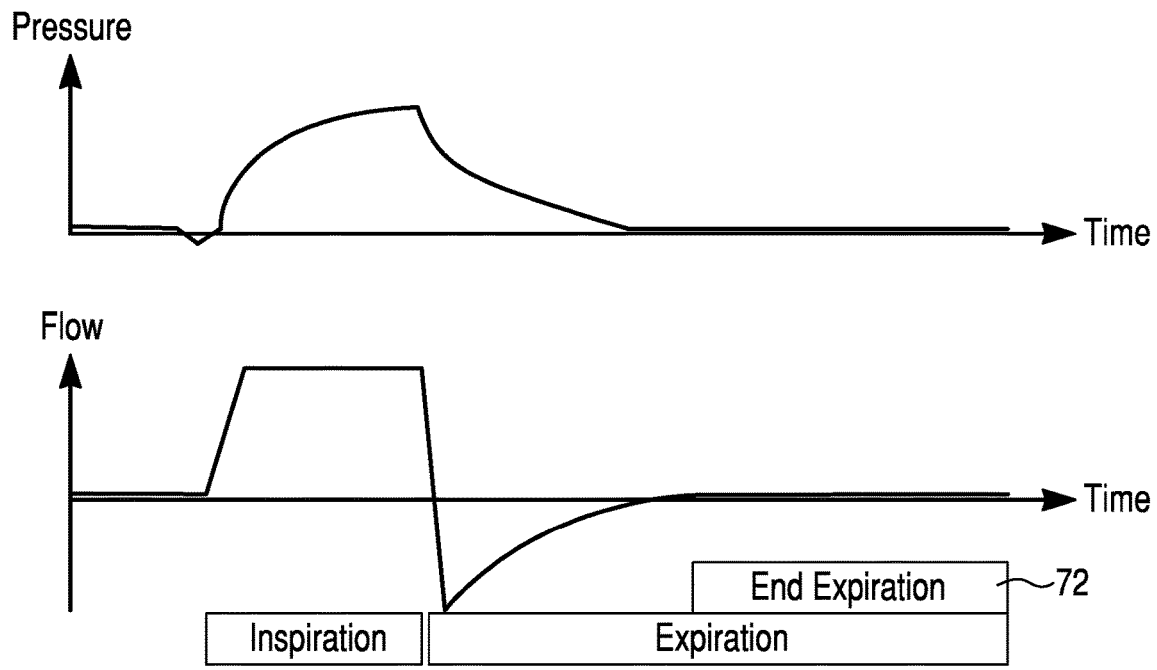
FIG. 6 shows airway pressure and airway flow curves and illustrates the inspiration, expiration, and end-expiration phases during mechanical ventilation, according to an exemplary embodiment.

FIG. 6 illustrates exemplary airway pressure and airway flow curves during inspiration and expiration phases of a breath. A patient may exhibit such pressure and flow curves while intubated and being assisted by a ventilator. Electrical pulses 76 shown in FIGS. 7-9 may be delivered to a patient by a diaphragm pacing system, for example, during end-expiration phases 72 of one or more breaths, during which background flow and pressure values remain relatively constant.

FIGS. 7-9 illustrate exemplary nerve stimulation patterns that may be used to test electrode combinations, which may include development of all or a portion of a recruitment curve for each electrode combination. Electrode combinations may be tested to locate optimal electrodes for the desired result, such as phrenic nerve stimulation to pace the diaphragm. The nerve stimulation patterns illustrated in FIGS. 7-9 may be implemented during any of the various stages of the algorithms described herein, such as during the testing of electrode combinations described in connection with FIGS. 13-14C. For some electrode combinations, the stimulation patterns may be implemented to develop full recruitment curves, such as those shown in FIGS. 5, 10A, and 10B.

FIGS. 7-9 are generalized to show electrical pulses 76 delivered over a period of time (x-axis) and each having a certain stimulation charge (y-axis). However, the stimulation charge of each pulse 76 may be varied as a function of current amplitude, pulse width (the length of time current is applied), voltage, or a combination of these parameters. For example, referring back to FIG. 5, to achieve the increase in charge shown along the x-axis, successive electrical pulses 76 may be applied for different amounts of time while the current amplitude may be held constant. The pulse widths of individual pulses may therefore increase along the x-axis of FIG. 5. Alternatively, to achieve the increase in charge shown along the x-axis, different current amplitudes may be applied during successive pulses 76 while the pulse width may be held constant. Similarly, voltage may be increased or decreased to increase or decrease charge. Accordingly, the diaphragm pacing systems and methods described herein may vary pulse width, current amplitude, or voltage, or a combination, to achieve varying charge levels.

As shown in FIG. 7, electrical pulses 76 may be delivered in a variety of patterns. In one embodiment, the diaphragm pacing system may include at least three stimulation modes: Stim. Mode 1, Stim. Mode 2, and Stim. Mode 3. In a first pattern, referred to as Stim. Mode 1, successive pulses 76 may be delivered during a single end-expiration phase 72. In one embodiment, each pulse 76 of Stim. Mode 1 may increase in charge relative to the previous pulse 76. As described above, the increase in charge may be due to a larger pulse width, larger current, larger voltage, or a combination of changes among these parameters. Six electrical pulses may be delivered during each end-expiration phase 72. However, in other embodiments, less than or more than six electrical pulses may be delivered during an end-expiration phase 72, and in one embodiment, three electrical pulses may be delivered during an end-expiration phase 72. The diaphragm response to the pulses 76 of Stim. Mode 1 may allow for development of a recruitment curve for the specific electrode combination. For example, the pulses 76 of Stim. Mode 1 may allow the system to determine the activation threshold and the maximal recruitment level of a nerve when stimulated with the tested electrode combination.

FIG. 7 further illustrates a second stimulation pattern, referred to as Stim. Mode 2. In Stim. Mode 2, similar to Stim. Mode 1, electrical pulses 76 may be delivered during end-expiration phases 72. However, in Stim. Mode 2, successive electrical pulses 76 may have charge values that are closer together than the charge values of successive pulses of Stim. Mode 1. Having successive pulses 76 with more closely spaced charge values may allow for a more accurate determination of the recruitment curve corresponding to the tested electrode combination. For example, relative to the pulses shown in Stim. Mode 1 of FIG. 7, the pulses shown in Stim. Mode 2 of FIG. 7 may allow more accurate determinations of the activation threshold and the maximal recruitment level.

A third stimulation pattern is shown as Stim. Mode 3 of FIG. 7. In this example, the pulses 76 in a single end-expiration phase 72 may each have the same charge value, although the charge value of pulses 76 in different end-expiration phases 72 may be different. For example, the charge value of pulses 76 in a later end-expiration phase may be greater than the charge value of pulses 76 in an earlier end expiration phase. Applying multiple pulses 76 having the same charge during a single end-expiration phase 72 may allow the diaphragm response to that electrode combination and charge to be measured multiple times. The system may take an average or use algorithms to eliminate abnormal responses, allowing for a more accurate determination of the diaphragm response to the specific electrode combination and charge.

The number of pulses delivered during an end-expiratory phase 72, in any Stim. Mode, may be based at least in part on one or more of the following factors: a) the duration of the end-expiratory phase, b) the maximum rate at which the diaphragm pacing system can stimulate, and c) the duration of the diaphragm response (e.g., the change in pressure, air flow, volume, chest acceleration, etc., caused by each pulse 76). The optimal number of pulses 76 delivered during an end-expiratory phase (the optimal rate of stimulation), may be determined by considering one or more of these factors. As just one illustrative example, stimulation pulses 76 may be delivered at a rate of 4 Hz to allow 250 ms between pulses 76, which may be slightly longer than the time it takes for the pressure and air flow waves caused by the pulse 76 and its resulting diaphragm response to peak and fade away, without overlapping with the next diaphragm response. However, the frequency of pulse delivery can be higher or lower than 4 Hz and may be varied in accordance with numerous considerations and testing conditions. Optimizing the rate of stimulation during mapping may minimize the overall time required to select the optimal electrodes for nerve stimulation by using the highest possible frequency that will still allow for accurate diaphragm response measurements.

FIG. 8 illustrates the exemplary stimulation patterns of FIG. 7 with a graph depicting flow during inspiration and expiration phases. In one embodiment, the flow shown in FIG. 8 is of a patient receiving breathing assistance from a ventilator. As can be seen in FIG. 8, the pulses 76 of the various stimulation modes may be delivered during end-expiration phases 72, when background flow is relatively constant (and close to zero).

FIG. 9A illustrates exemplary flow, stimulation charge, diaphragm response, pulse width, and current level during four breaths of a patient. During these four breaths, the patient may be receiving breathing assistance from a ventilator, and testing of electrode combinations may occur during the end-expiration phases 72 (individually, 72a, 72b, 72c, and 72d) of the ventilator-assisted breaths. Flow is illustrated at the top of FIG. 9A. The stimulation charge of electrical pulses 76 is illustrated just below the flow signal. The electrical pulses 76 of the diaphragm pacing system may affect flow during the end-expiration phases. The diaphragm response to the electrical pulses 76 is shown below the stimulation charge portion of FIG. 9A. The diaphragm response may be measured as a change in flow, pressure, or other parameter in response to the electrical pulses 76. The pulse width of each electrical pulse 76, which is the length of time each pulse 76 is applied, is also shown in FIG. 9A. Finally, at the bottom of FIG. 9A, the current level of each pulse width is illustrated. As can be seen by comparing the stimulation charge, pulse width, and current level graphs of this example, the stimulation charge may be varied during a single end-expiration phase by modifying the pulse width, while current during the same end-expiration phase may remain constant.

The diaphragm response may aid the pacing system in modifying the electrical pulses 76 to extract more accurate information about the activation threshold and maximal recruitment level of the nerve when stimulated with the tested electrode combination. For example, referring to end-expiration phase 72a in FIG. 9A, the diaphragm response is low and relatively steady in response to the first four pulses 76 and then increases in response to the fifth pulse 76. Accordingly, the activation threshold of the nerve may be somewhere between the charge levels of the fourth and fifth pulses 76 of phase 72a.

To determine a more narrow range for the activation threshold, the pulses 76 delivered during the second end-expiration phase 72b may all fall within a more narrow range than the range encompassing the charges of phase 72a. Similarly, the pulses 76 delivered during the third end-expiration phase 72c may all fall within a more narrow range of charges. For example, each pulse 76 delivered during phase 72b may have a charge between the charges of the third and fifth pulses delivered during phase 72a. Each pulse 76 delivered during phase 72c may have a charge higher than the charge of the fifth pulse of phase 72a, with the charge difference between consecutive pulses 76 being similar to the charge difference between consecutive pulses 76 of phase 72b. In this manner, the system may determine a more accurate estimate of the activation threshold AT, which may be, for example, the stimulation charge of the third pulse of phase 72b (corresponding to an increase in the diaphragm response during phase 72b).

During phase 72c, the diaphragm response in this example increases proportionally in response to increases in stimulation charge. Accordingly, these charges may fall within the proportional recruitment section of a recruitment curve similar to that of FIG. 5. Finally, the electrical pulses 76 delivered during the fourth end-expiration phase 72d may be used to determine the maximal recruitment level and supramaximal recruitment portion of the recruitment curve. As can be seen in the diaphragm response portion corresponding to phase 72d, the diaphragm response saturates and remains steady and high during phase 72d, even though the stimulation charge of each pulse 76 is increasing.

FIG. 9B illustrates exemplary flow, pressure, EMG, and acceleration measurements, as determined by one or more sensors 12, 14, in response to electrical pulses 76. Flow, pressure, EMG activity, and acceleration (e.g., of the chest wall) may be indicative of the diaphragm's response to electrical pulses 76. As can be seen in FIG. 9B, pressure may drop in response to stimulation charges above the activation threshold because the diaphragm responds by contracting, which results in expansion of the lungs. EMG activity may increase because the diaphragm muscle has been electrically stimulated. Acceleration of the chest wall or other portion of the patient may increase when pulses 76 are above the activation threshold and the diaphragm is stimulated, expanding the lungs and the chest.

In one embodiment, the diaphragm pacing system is a constant-current system that may deliver pulses 76 having pulse widths within a defined range. In one example, the defined range for pulse widths is 10-300 μs. In various embodiments, the current may be between 0.1 mA and 10 mA, 0.25 mA and 5 mA, or 0.5 mA and 2 mA, and in one example is 1 mA. It may therefore be useful if the pulse width of a pulse 76 at or near the activation threshold PW(AT) is within a specific range R, such as the range R shown in hatching in FIG. 9A. Range R may be a portion, such as the first 20%, of the full pulse width range. In one embodiment, range R is 10-68 µs. The diaphragm pacing system may therefore modify the current level of pulses 76, as shown between end-expiration phases 72a and 72b, to achieve an activation threshold pulse width PW(AT) within range R.

FIGS. 10A and 10B illustrate exemplary recruitment curves that may be developed based on the electrode combination testing of FIG. 9A. Referring to FIG. 10A, at shorter pulse widths (e.g., the first two pulses delivered during end-expiration phase 72b of FIG. 9A), the diaphragm response may be zero or close to zero. This portion corresponds to the zero recruitment portion of the recruitment curve. As pulse width increases (e.g., all pulses delivered during end-expiration phase 72c of FIG. 9A), the diaphragm response may increase generally proportionally. This section of the curve corresponds to the proportional recruitment section of the curve. Finally, when pulse width is above a certain level (e.g., all pulses delivered during end-expiration phase 72d of FIG. 9A), the diaphragm response may saturate at its maximum capacity and no longer increase, corresponding to the supramaximal recruitment portion of the recruitment curve. A line of best fit may be calculated using the data points corresponding to the pulse width of pulses 76 (x-axis) and their resulting diaphragm responses (y-axis).

To develop the recruitment curve of FIG. 10B, testing of a particular electrode combination may be carried out multiple times and the data points corresponding to tested pulse widths and their elicited diaphragm responses may be averaged. For example, the process of FIG. 9A, which takes place during four breaths, may be repeated one or more times during other sets of breaths. The data points may then be averaged, and a line of best fit may be calculated using the averages.

Mapping Process Exemplary Embodiment

FIGS. 11-14C will be referenced to describe an exemplary embodiment of a process of testing multiple electrode combinations to determine the optimal electrode combinations for nerve stimulation. For each tested electrode combination, electrical pulses 76 may be delivered to a nerve as described above, and the diaphragm pacing system may be capable of developing a recruitment curve that corresponds to that specific electrode combination and its effect on the target nerve.

Embodiments of the present disclosure provide systems capable of rapidly and automatically optimizing the delivery of stimulation via any multi-electrode pacing catheter such as, for example, the catheter described in U.S. Provisional Application No. 61/907,993 filed Nov. 22, 2013, titled "Apparatus for Assisted Breathing by Transvascular Nerve Stimulation and Related Methods," and U.S. application Ser. No. 14/550,485, filed Nov. 21, 2014, titled "Apparatus and Methods for Assisted Breathing by Transvascular Nerve Stimulation," the disclosures of which are incorporated herein. One embodiment provides a method for iteratively evaluating and selecting a subsection of suitable stimulation electrodes in an automated fashion. Stimulation delivery may be optimized by the selection of an appropriate subsection of electrodes suitable for nerve stimulation without requiring the movement of a satisfactorily-inserted catheter. A catheter may be satisfactorily inserted if some, or all, of its electrodes are able to produce charge fields that intersect a portion of at least one target nerve.

The iterative evaluation of electrode combinations described in connection with FIGS. 11-14C may save time during electrode selection by quickly focusing on electrode combinations most likely to provide a satisfactory diaphragm response. First, a subset of electrode combinations along the length of an elongated body 4, referred to as primary combinations (see FIG. 11), may be tested to determine the general location of a nerve relative to the elongated body 4. It may not be necessary to test all possible electrode combinations to determine the general location of the nerve. Then, based on the localized subset of primary electrode combinations in proximity to the nerve, additional combinations of electrodes, referred to as secondary electrode combinations, may be tested (see FIG. 12). Localizing a specific area of the elongated body 4 and then determining additional electrode combinations may prevent having to test numerous permutations of electrode combinations along the entire length of the elongated body 4.

The system may rapidly converge upon a suitable electrode combination, and its corresponding stimulation parameters, by analyzing and comparing the diaphragm's response to stimulation delivered across a range of electrode combinations. The system may also take into consideration physiological parameters such as Heart Rate, ECG, central venous pressure, etc. and discard electrode combinations or stimulation configurations that manifest undesirable effects of stimulation, including, but not limited to the stimulation of vagus nerve(s), which may be anatomically located close to the targeted zones (FIG. 1), the Sinoatrial node, etc. A variety of stimulation patterns can be used for the purpose of comparing responses, such as the patterns described above in connection with FIGS. 7-9. A multitude of sensors and signal artifacts can be used to quantify the physiological response to a stimulation including, but not limited to: electromyography, accelerometers placed in/on body, central venous pressure, blood oxygen saturation, carbon dioxide concentration, catheter position/depth within vein, mechanical movement, airway flow, and airway pressure.

In one embodiment, stimulation control unit 8 may perform an iterative process of testing and ranking of electrode combinations to converge onto a suitable electrode combination. By delivering ramps of stimulation to increasingly smaller sets of electrode combinations, the best electrode combination may be identified while reducing the overall time required and charge delivered to the body during the mapping process.

Figure 11:
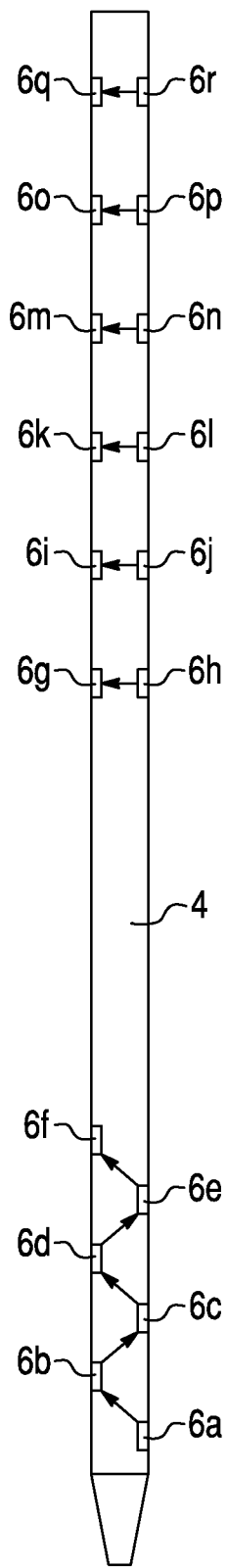
FIG. 11 is an example of preconfigured electrode pairs used in a first stage of an algorithm to identify a localized area of the catheter that is likely located anatomically closest to a target nerve, according to an exemplary embodiment.
Figure 12:
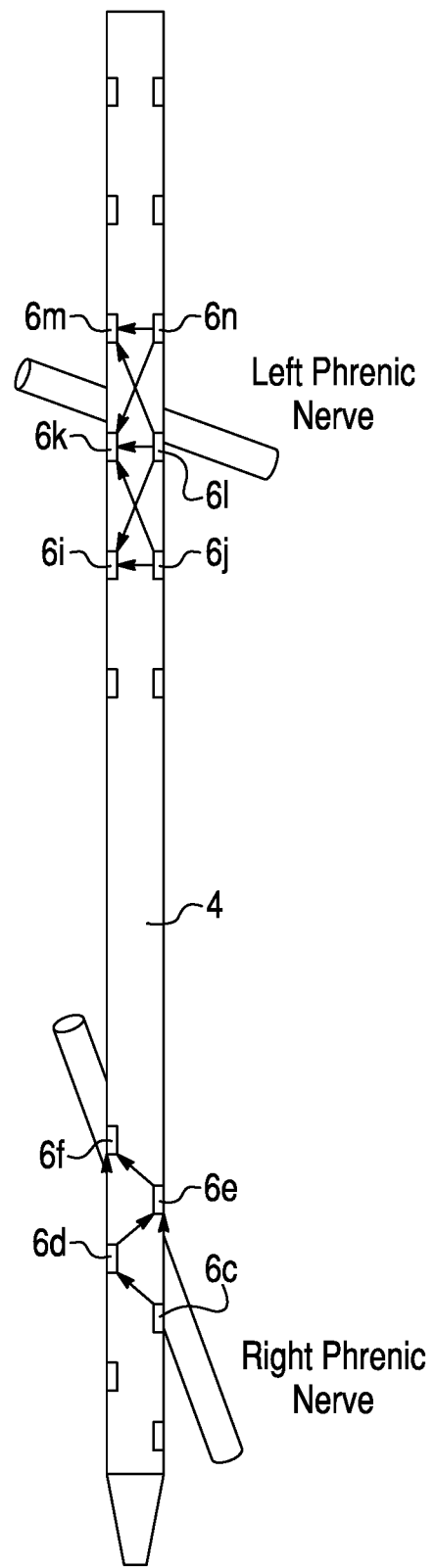
FIG. 12 is an example of a second stage of the algorithm during which all the electrodes within the identified catheter zone in stage one are evaluated, according to an exemplary embodiment. One goal may be to identify the optimal electrode combinations.

In a first stage, the algorithm may identically stimulate a series of configurable electrode combinations that are expected to be suitably oriented in relation to the phrenic nerve. FIG. 11 provides an example of preconfigured electrode combinations. The physiological response can be described as the summed-total perturbations in any signal artifact caused by the entire train of stimulation. Based on the comparative desirable and undesirable physiological response elicited, the algorithm may identify a location on the inserted catheter that is likely located close to the nerve. Electrode combinations within this identified catheter area, such as those shown in FIG. 12, are likely to be optimal for stimulation delivery.

In a second stage, the electrodes within this identified area may be stimulated with a ramp of stimulation and comparatively evaluated based on the elicited physiological response. The physiological response to stimulation delivery can be quantified by a multitude of signals including, but not limited to, electromyography, accelerometers placed in/on body, central venous pressure, blood oxygen saturation, carbon dioxide concentration, catheter position/depth within vein, mechanical movement, airway flow, and airway pressure. In one embodiment, the airway pressure may be used to quantify the response of the diaphragm to a round of end-expiration stimulation (e.g., as shown in FIG. 8). A comparison of the responses elicited by the electrode combinations during this stage yields a potential multitude of optimal electrode combinations for stimulation. This multitude of optimal combinations can subsequently be configured such that they all, or a subsection, of them are used for stimulation delivery during pacing.

FIG. 13 illustrates a general overview of a process for determining optimal electrode combinations for nerve stimulation. In step 1310, a first plurality of electrode combinations along the length of an elongated body 4, such as a catheter, may be tested for their ability to stimulate a target nerve. As noted above, this process may aid in locating the section of the catheter that is closest to the target nerve. FIG. 11 corresponds to step 1310, and the arrows in FIG. 11 indicate exemplary primary electrode combinations (shown as pairs) that may be tested to determine which portion of the catheter is closest to the target nerve or nerves. In one embodiment, six proximal electrode combinations may be tested during step 1310 to determine their effect on a left phrenic nerve (e.g., 6g/6h, 6i/6j, 6k/6l, 6m/6n, 6o/6p, and 6q/6r). Similarly, six distal electrode combinations may be tested during step 1310 to determine their effect on a right phrenic nerve (e.g., 6a/6b, 6b/6c, 6c/6d, 6d/6e, and 6e/6f). However, different proximal or distal primary electrode combinations may additionally or alternatively be tested, and less than six or more than six combinations may be tested during step 1310. After various electrode combinations have been tested, the stimulation control unit 8 may determine, based on the diaphragm response to stimulation from the tested combinations, which section or sections of the catheter are located closest to the target nerve or nerves.

In step 1320, a second plurality of electrode combinations identified in step 1310 may be further tested and ranked to determine their suitability for nerve stimulation. The second plurality of electrode combinations may include a subset of the electrode combinations, within a localized area, as well as additional secondary electrode combinations. FIG. 12 corresponds to step 1320 and illustrates various electrode combinations (shown as pairs) that may be further tested. In one example, the testing of step 1320 results in identification of one or more proximal electrode combinations as most suitable for stimulation of the left phrenic nerve and identification of one or more distal electrode combinations as most suitable for stimulation of the right phrenic nerve.

In step 1330, the suitable electrode combinations identified in step 1320 may be tested further, and a recruitment curve, such as the recruitment curves shown in FIGS. 5, 10, and 11, may be developed for each of the combinations.

Figure 14A:
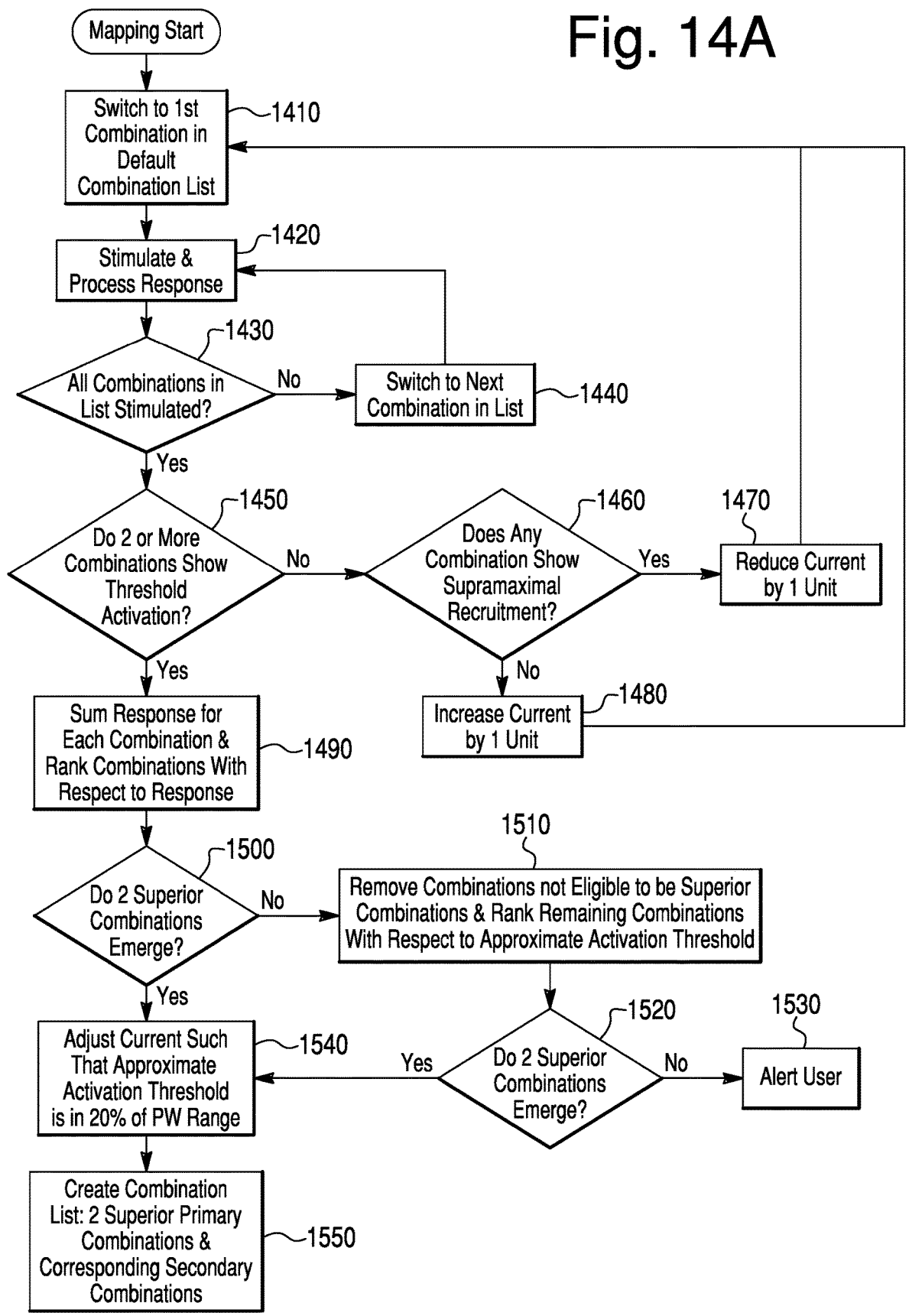
FIG. 14A shows a flowchart of a first stage of the mapping algorithm of FIG. 13, according to an exemplary embodiment.
Figure 14B:
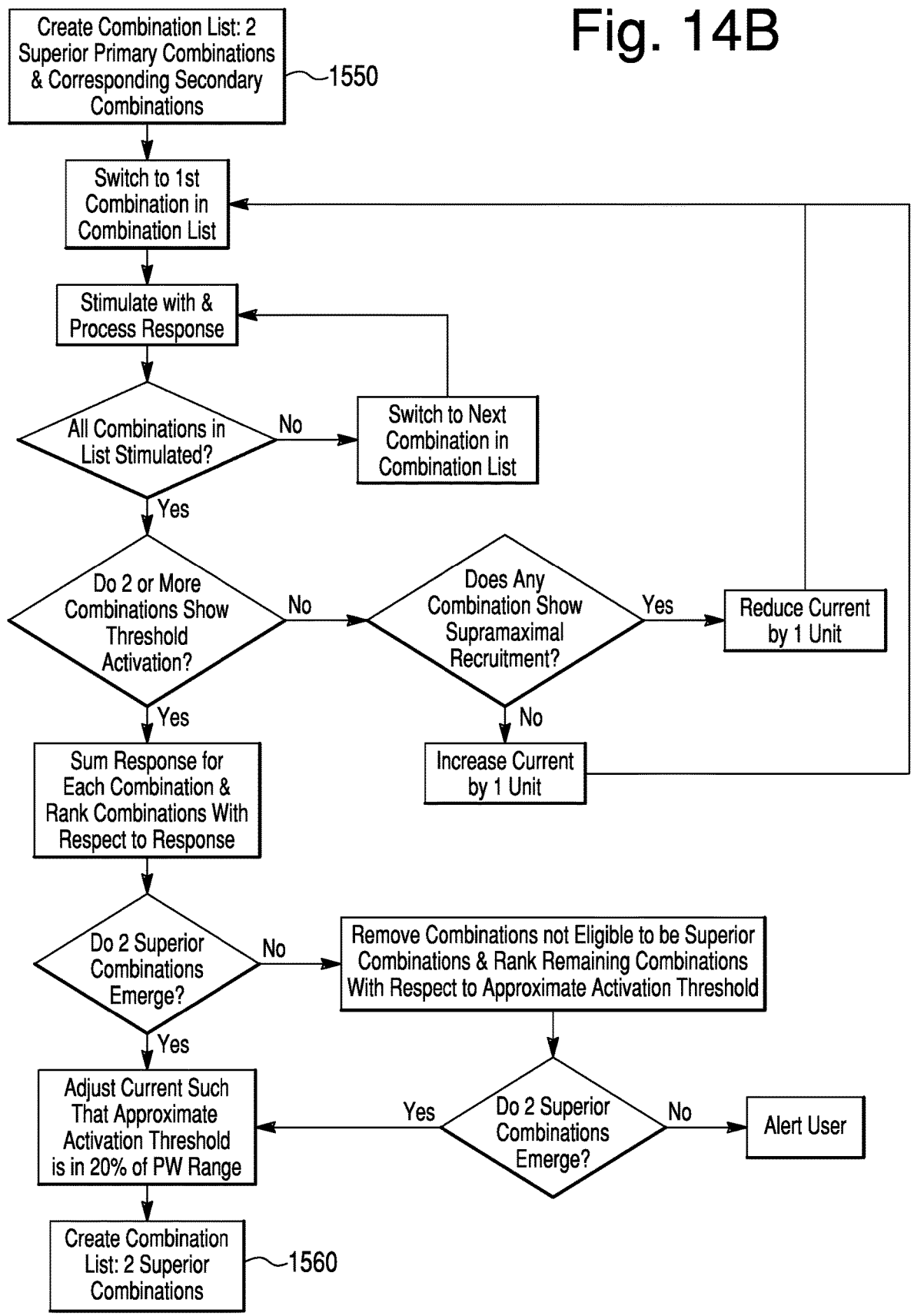
FIG. 14B shows a flowchart of a second stage of the mapping algorithm of FIG. 13, according to an exemplary embodiment.
Figure 14C:
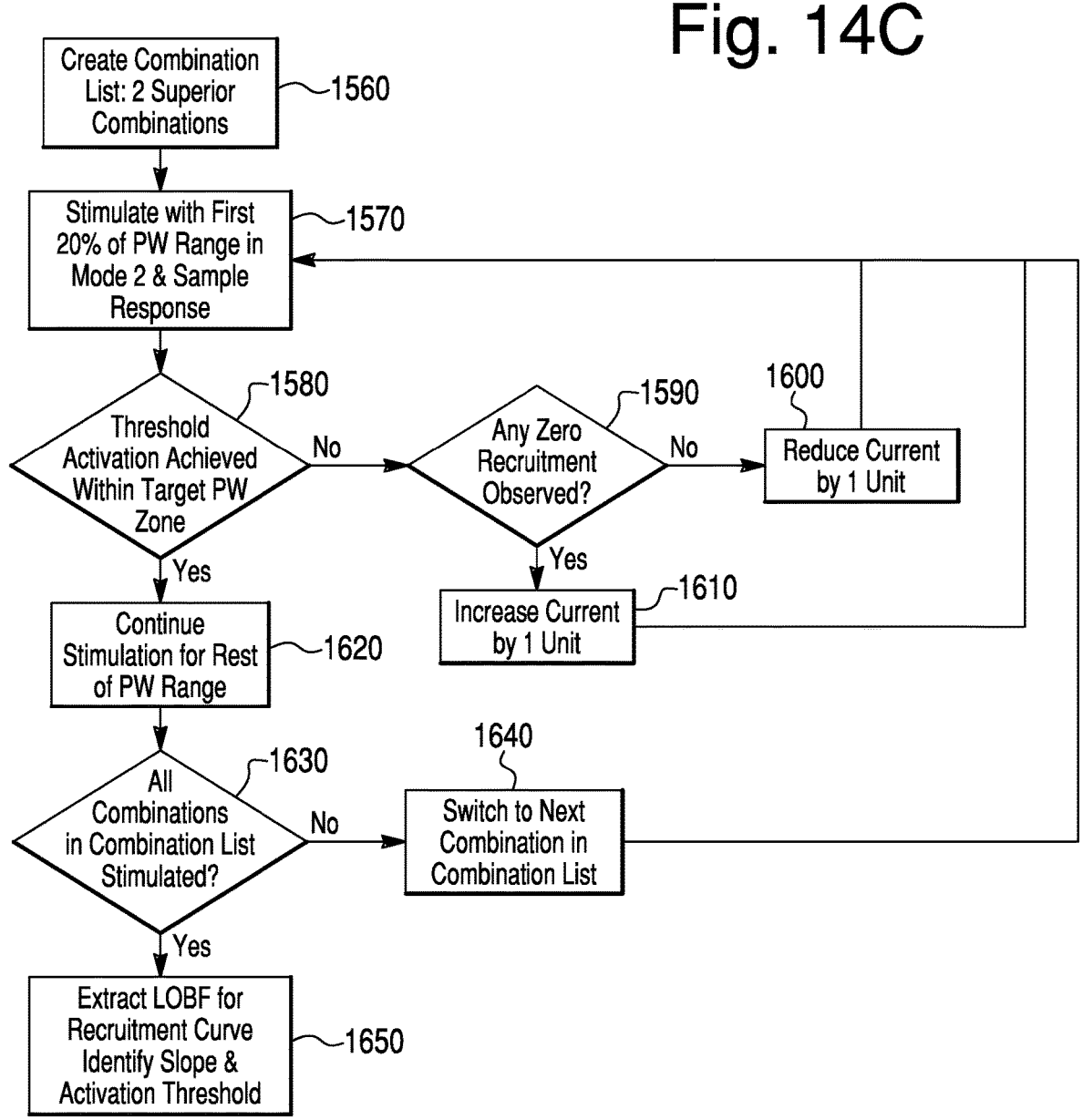
FIG. 14C shows a flowchart of a third stage of the mapping algorithm of FIG. 13, according to an exemplary embodiment.

FIGS. 14A-14C illustrate in greater detail the steps of FIG. 13. FIG. 14A corresponds to step 1310, FIG. 14B corresponds to step 1320, and FIG. 14C corresponds to step 1330.

In the first stage of the mapping process as shown in FIGS. 14A and 11, the stimulation may be delivered to preconfigured electrode combinations distributed on the elongated body 4. In this stage, one goal may be to identify a localized area of the catheter that is likely located anatomically closer to the target nerve. In one embodiment, the initial set of preconfigured electrode combinations does not include all possible electrode combinations along the length of the catheter. Electrode combinations likely to be close to the target nerve may be identified by comparing their summed-total response to the entire ramp of stimulation without necessarily considering the activation threshold or recruitment curve involved. Electrode combinations that result in the manifestation of undesirable physiological effects may be eliminated during this stage.

FIG. 14A illustrates in detail an algorithm for identifying the subsection of an elongated body 4 located in close proximity to the target nerve. In general, in steps 1410-1440, electrical pulses 76 may be delivered to electrode combinations, and the diaphragm response to each of the combinations may be processed. In step 1410, the system may select an electrode combination out of a first plurality of electrode combinations (also referred to herein as primary combinations). The first plurality of electrode combinations may be a preconfigured list programmed into the stimulation control unit 8. In one embodiment, the first plurality of electrode combinations may be the electrode pairs shown in FIG. 11. In steps 1410-1440, each of the electrode combinations may be stimulated one at a time.

In step 1420, a nerve may be electrically stimulated by delivering current to a first electrode combination of the first plurality of combinations. The current may be delivered as an electrical stimulation that includes one or more pulses 76, such as those shown in FIGS. 7-9, each having a pulse width and a current amplitude. Also in step 1420, the algorithm may monitor a patient's response to the electrical stimulation of the nerve. In one embodiment, one or more sensors 12 and/or one or more breath sensors 14 may be used to monitor the patient's response to stimulation. The sensors 12, 14 may provide information on, for example, the diaphragm response of the patient (e.g., by sensing flow, pressure, volume, mechanical movement, or any other parameters indicative of the diaphragm response), whether the electrical stimulation is causing undesired effects on other anatomical features (e.g., by sensing electromyographic activity or heart rate), or any other patient responses disclosed herein as measurable by sensors 12, 14.

In step 1430, the algorithm may determine whether all electrode combinations in the first plurality of electrode combinations have been stimulated. If all electrode combinations have not been stimulated, the algorithm may move to the next electrode combination in the first plurality of electrode combinations (step 1440) and proceed to stimulate and process the patient response to the next electrode combination (step 1420). In one embodiment, to save time, step 1420 may be halted for a specific electrode combination if the system has already found an electrode combination with a lower activation threshold.

When all of the electrode combinations of the first plurality of electrodes have been tested, the system may determine whether two or more of the first plurality of electrode combinations show threshold activation (step 1450). A combination may show threshold activation if the delivered electrical stimulation (e.g., a set of three electrical pulses 76) encompasses a range between a charge in which the diaphragm does not respond and a charge in which the diaphragm does respond. The response (or lack thereof) of the diaphragm may be measured, as described above, by one or more sensors 12, 14.

If two or more of the combinations do not show threshold activation, the system may determine whether any electrode combination shows supramaximal recruitment (step 1460). An electrode combination may show supramaximal recruitment if delivered electrical pulses of increasing charge do not cause an increase in diaphragm response. If an electrode combination shows supramaximal recruitment, the system may reduce the current amplitude by one unit (step 1470). If two or more of the combinations do not show threshold activation (step 1450), and none of the combinations cause supramaximal recruitment (step 1460), the current may be increased by one unit (step 1480). If two or more combinations show threshold activation (step 1450), the diaphragm responses for each electrode combination may be added, and the combinations may be ranked in accordance with their corresponding diaphragm responses (step 1490), as determined by one or more sensors 12, 14.

In step 1500, the system determines whether two superior primary electrode combinations emerge. An electrode combination may be superior relative to another electrode combination if its total elicited diaphragm response is greater than the total elicited diaphragm response of the other electrode combination. Thus, in step 1500, the system may determine whether two electrode combinations elicit a greater diaphragm response than the other electrode combinations. As noted elsewhere, the diaphragm response may be measured by or derived from information from one or more sensors 12, 14. In one embodiment, characteristics of the diaphragm response, such as response duration, response relaxation time, and response half decay time (e.g., of changes in flow, pressure, EMG signals, or other indicators of diaphragm response), may be used to rank electrode combinations and determine which combinations elicit greater diaphragm responses. If two superior combinations do not emerge, combinations may be removed if they are not eligible to be superior combinations (step 1510). Two superior combinations may not emerge if, for example, less than two combinations show activation threshold, or several combinations elicit diaphragm responses that are very close to each other. Electrode combinations may not be eligible, for example, if they cause stimulation of the vagus nerves or the Sinoatrial node, or cause any other undesirable effects as determined, for example, by one or more sensors 12, 14. The remaining combinations then may be ranked with respect to their corresponding activation thresholds (step 1510). In one embodiment, electrode combinations having lower activation thresholds are ranked more highly than electrode combinations having higher activation thresholds. A lower activation threshold may allow minimization of the charge delivered to the body during diaphragm pacing. After removal of unsuitable electrode combinations, the system may determine whether two superior combinations have emerged (step 1520). If two superior combinations do not emerge, the user may be notified (step 1530) for possible repositioning of the elongated body 4.

Alternatively, if two superior combinations do emerge, the current amplitude may be adjusted such that the approximate activation threshold may be achieved by a pulse 76 having a pulse width within the lowest 20% of the pulse width range. In other embodiments, the pulse 76 may have a pulse width within another segment of the pulse width range. This adjustment may allow systems with constraints on pulse width to implement testing and development of the full recruitment curve for the particular electrode combination and nerve.

Finally, the algorithm of FIG. 14A may result in determination of a list of: a) superior primary electrode combinations, and b) corresponding secondary combinations (step 1550). The primary electrode combinations may be a subset of the first plurality of electrode combinations that were found, through the algorithm of 14A, to elicit a suitable diaphragm response and to be eligible to be a superior combination. A suitable diaphragm response, which may be higher than the diaphragm response of other electrode combinations, may be an indicator of proximity to the nerve. The corresponding secondary combinations may be determined by the system based on the electrodes within the superior primary electrode combination subset.

For example, referring to FIG. 12, electrode pairs 6k/6l and 6m/6n are exemplary superior primary electrode combinations, and the remaining pairs, indicated by arrows, are the corresponding secondary combinations formed based on the superior primary combinations. Other primary electrode pairs that are not superior primary combinations, such as 6i/6j, may be included in the set of secondary combinations because of their proximity to the superior primary combinations. For example, if superior primary combination 6k/6l is ranked the highest, adjacent electrodes 6i/6j may be included in the set of secondary combinations for further testing, even though 6i/6j was tested previously as a primary combination. When tested again, different stimulation parameters may be used based on the diaphragm responses obtained during testing of the primary combinations. The superior primary and corresponding secondary combinations (step 1550) may together be referred to as a second plurality of electrode combinations. Developing the second plurality of electrode combinations from the localized subset of the first plurality of electrode combinations may prevent having to test a greater variety of combinations, such as those shown in FIG. 12, along the length of the catheter.

Accordingly, in one embodiment, the output of step 1550 (FIG. 14A) and step 1310 (FIG. 13) may be a second plurality of electrode combinations. The second plurality of electrode combinations may include two primary electrode combinations (e.g., two combinations that were tested during the algorithm of FIG. 14A) and their corresponding secondary combinations (e.g., various other electrode combinations that may be formed based on the electrodes of the primary combinations). In other embodiments, the output of step 1550 and 1310 is less than or more than two superior primary electrode combinations, such as one, three, five, or more primary electrode combinations, and any number of corresponding secondary combinations.

The algorithm described in connection with FIGS. 14A-14C may be carried out by a diaphragm pacing system to select electrodes for stimulating a single nerve. In one embodiment, the process may be repeated to select optimal electrodes for stimulating a second nerve. For example, if the diaphragm pacing system includes an electrode assembly 2 as described in connection with FIGS. 1 and 3, the process of FIGS. 14A-14C may be implemented a first time to determine optimal proximal electrodes for stimulation of a left phrenic nerve and a second time to determine optimal distal electrodes for stimulation of a right phrenic nerve.

In one embodiment, however, if the mapping process is carried out to select the optimal electrodes for stimulating the left phrenic nerve and the right phrenic nerve, testing of proximal and distal electrodes may be done in parallel. In this embodiment, the process of FIGS. 14A-14C is carried out on both the proximal and distal sets of electrodes, but electrical stimulation may be delivered to both left and right phrenic nerves during the same end-expiratory phase or phases. Stimulation pulses 76 may alternate between an electrode combination for stimulating the left phrenic nerve and an electrode combination for stimulating the right phrenic nerve, allowing testing and accurate monitoring of both combinations during a single breath or breaths. In yet another embodiment, the left and right phrenic nerves may be tested simultaneously, with the process of FIGS. 14A-14C carried out on both the proximal and distal sets of electrodes. Unilaterally placed sensors 12, 14, such as accelerometers, may be used to separately monitor the individual hemi-diaphragm responses to simultaneous pulses 76 stimulating each nerve, and in some embodiments, determine the separate contributions of the left and right phrenic nerve stimulations.

Referring to FIG. 14B, which illustrates step 1320 of FIG. 13, the second plurality of electrode combinations determined in step 1550 of FIG. 14A may be further tested and ranked. The intermediate steps of FIG. 14B are similar to those of FIG. 14A and therefore are not repeated here. However, the output of the algorithm of FIG. 14B (step 1560) may be a subset of the second plurality of electrode combinations. In one embodiment, the output of FIG. 14B may be two electrode combinations for stimulation of a nerve, although the output may be a single electrode combination or more than two electrode combinations. If the output is two electrode combinations, both combinations may be used to stimulate the same nerve, as shown in FIGS. 4A and 4B.

Referring to FIG. 14C, which illustrates step 1330 of FIG. 13, the combinations identified in step 1560 of FIG. 14B may be further tested. In step 1570, electrical pulses 76 (stimulation) may be delivered having pulse widths within the first 20% of the full pulse width range (the 20% portion may be the range R shown in FIG. 9A), and the diaphragm response may be determined by one or more sensors 12, 14. In one embodiment, the diaphragm pacing system may be in Stim. Mode 2 during step 1570, although other modes and stimulation patterns may be used during this step. If the threshold activation is not achieved within the target pulse width range R (step 1580), the current may be reduced or increased depending on whether any zero recruitment is observed (steps 1590, 1600, and 1610). If threshold activation within the target pulse width range R is achieved (step 1580), stimulation may be continued for the full pulse width range (step 1620). The system may determine whether all combinations have been tested (step 1630) and iterate until each combination has been tested (step 1640). Finally, the system may extract the line of best fit for the data points corresponding to one or more of the tested electrode combinations and identify the slope and activation threshold for the tested combinations (step 1650). The line of best fit may be a recruitment curve, such as those shown in FIGS. 5, 10A, and 10B, corresponding to the tested electrode combination and nerve.

In one embodiment, electrode combinations with recruitment curves having a greater slope along the proportional recruitment section are selected for nerve stimulation over electrode combinations with recruitment curves having a smaller slope along the proportional recruitment section. A greater slope along the proportional recruitment section may allow testing for maximal recruitment to be completed more quickly. In addition, electrode combinations having a more constant slope along the proportional recruitment section may be selected for nerve stimulation over combinations having a more variable slope because a straight proportional recruitment section may simplify the control of nerve stimulation.

In one embodiment, the electrode combinations tested in steps 1310 and 1320 of FIG. 13 (also see FIGS. 14A and 14B) are stimulated with electrical pulses 76 having a consistent ramp of stimulation. Rankings may be in accordance with the summed-total response to the consistent ramp of stimulation. Accordingly, Stim. Mode 1, as shown in FIG. 8, may be used in these first two stages of mapping. In Stim. Mode 1, each train of stimulation may be constrained to a single end-expiration phase. Once the best electrode combinations have been determined, the system may stimulate nerves using those electrode combinations, analyze the diaphragm response to each combination, and extract a recruitment curve corresponding to each combination.

Figure 15:
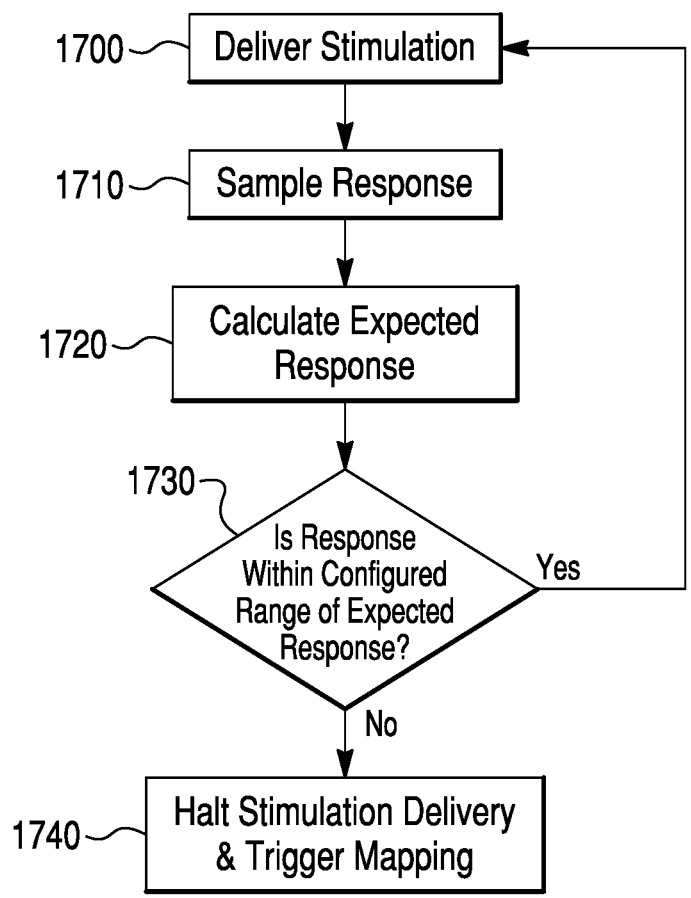
FIG. 15 shows a flowchart of a supervisory algorithm, according to an exemplary embodiment.

Referring to FIG. 15, another embodiment provides a method for monitoring the performance of pacing delivered using the diaphragm pacing system. Testing during the mapping processes described above (to select the optimal electrode combinations) may be carried out at a lower frequency than the frequency used for later diaphragm pacing with those selected electrode combinations. The diaphragm pacing system therefore has information, obtained during the mapping process, that can be used to predict the body's response to the actual diaphragm pacing. The method of FIG. 15 may autonomously rectify a degradation of performance via the use of the mapping and recruitment curve generation methods described herein. The method may include the constant quantification of the response of the body to a round of stimulation delivered (steps 1700, 1710, and 1720). If the response evoked is not that which is expected for a stimulation pulse configured based on a previously acquired recruitment curve (step 1730), the system may automatically halt stimulation and reexecute the mapping process of FIG. 13 (step 1740). In one embodiment, muscle fatigue, muscle strengthening, or catheter movement may cause the response of the diaphragm during pacing to be inconsistent with the expected response. One embodiment may include a stimulation control unit 8 that triggers the mapping and recruitment curve generation process at configurable intervals (e.g., at preset time intervals), or if it detects any anomalies in the physiological response relative to the expected physiological response.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

The invention claimed is:

1. A method for determining a recruitment relationship, the method comprising:
    assisting a plurality of breaths of a patient with a ventilator;
    inserting a plurality of electrodes into a patient, wherein the plurality of electrodes include an electrode combination;
    emitting a plurality of stimulation pulses from the electrode combination;
    measuring responses of at least one respiratory muscle to the plurality of stimulation pulses;
    based on the measured respiratory muscle responses, determining a first range of charges that includes a nerve activation threshold and a second range of charges within a proportional recruitment section;
    developing the recruitment relationship based on at least the first and second ranges of charges, wherein the recruitment relationship defines a relationship between a charge of a stimulation pulse and a respiratory muscle response; and
    after developing the recruitment relationship:
    a) stimulating the at least one respiratory muscle with the electrode combination, b) using the recruitment relationship, determining an expected respiratory muscle response to the stimulation, and c) comparing an actual respiratory muscle response to the expected respiratory muscle response.

2. The method of claim 1, further including, based on the measured respiratory muscle responses, determining a third range of charges that includes a maximal recruitment level of the recruitment relationship;

wherein the recruitment relationship is based on at least the first, second, and third ranges of charges.

3. The method of claim 1, wherein the at least one respiratory muscle includes a diaphragm.

4. The method of claim 1, wherein the recruitment relationship applies to charges that were emitted and charges that were not emitted.

5. The method of claim 1, wherein each pulse of a portion of the plurality of stimulation pulses increases in charge relative to a previous pulse.

6. The method of claim 1, wherein a first portion of the plurality of stimulation pulses includes pulses having a first same charge, a second portion of the plurality of stimulation pulses includes pulses having a second same charge, the second same charge being higher than the first same charge, and a third portion of the plurality of stimulation pulses includes pulses having a third same charge, the third same charge being higher than the second same charge.

7. The method of claim 1, wherein the electrode combination is a first electrode combination, and the plurality of breaths is a first plurality of breaths, and the method further includes repeating the emitting step, the measuring step, and the determining step with a second electrode combination of the plurality of electrodes during a second plurality of breaths.

8. The method of claim 1, wherein at least one pulse of the plurality of stimulation pulses does not cause a respiratory muscle response.

9. The method of claim 1, wherein the expected respiratory muscle response is no response.

10. The method of claim 1, further comprising, if the actual respiratory muscle response differs from the expected respiratory muscle response, halting stimulation of the at least one respiratory muscle with the electrode combination and re-executing the steps of emitting a plurality of stimulation pulses, measuring respiratory muscle responses, determining the first range and the second range, and developing the recruitment relationship.

11. The method of claim 1, further comprising, at preset time intervals, halting stimulation of the at least one respiratory muscle with the electrode combination and re-executing the steps of emitting a plurality of stimulation pulses, measuring respiratory muscle responses, determining the first range and the second range, and developing the recruitment relationship.

12. The method of claim 1, wherein respiratory muscle response includes at least one of a change in: airway pressure, airway flow, electromyography, chest wall movement, central venous pressure, blood oxygen saturation, carbon dioxide concentration, or chest wall acceleration.

13. The method of claim 1, wherein inserting a plurality of electrodes into a patient includes inserting a plurality of electrodes into a blood vessel.

14. The method of claim 1, wherein determining the recruitment relationship includes determining a charge causing zero recruitment of a respiratory nerve that activates the at least one respiratory muscle.

15. The method of claim 14, wherein the respiratory nerve is a phrenic nerve.

16. The method of claim 1, wherein the at least one respiratory muscle includes a diaphragm.

17. The method of claim 7, wherein the method further comprises positioning a first portion of the plurality of electrodes proximate a left phrenic nerve and positioning a second portion of the plurality of electrodes proximate a right phrenic nerve.

18. The method of claim 17, wherein the first portion of the plurality of electrodes includes the first electrode combination, and the second portion of the plurality of electrodes includes the second electrode combination.

19. The method of claim 1, wherein determining a recruitment relationship includes calculating a line of best fit for a set of data points, and where each data point of the set of data points represents a respiratory muscle response to a corresponding charge.

20. The method of claim 1, wherein determining a recruitment relationship includes calculating a line of best fit for a set of data points, and where each data point of the set of data points represents an average of respiratory muscle responses to corresponding charges.

21. A method for determining a recruitment relationship, the method comprising:

assisting a plurality of breaths of a patient with a ventilator;

positioning a plurality of electrodes at a location for stimulating at least one respiratory muscle, wherein the plurality of electrodes include an electrode combination;

emitting a plurality of stimulation pulses from the electrode combination;

measuring responses of at least one respiratory muscle to the plurality of stimulation pulses;

based on the measured respiratory muscle responses, determining a first charge corresponding to a nerve activation threshold, a second charge corresponding to a maximal recruitment level, and at least one charge within a proportional recruitment section; and developing the recruitment relationship based on the at least one charge, and one or more of the first change or the second charge;

wherein the recruitment relationship defines a relationship between a charge of a stimulation pulse and a respiratory muscle response.

22. The method of claim 21, further comprising, after developing the recruitment relationship:

a) stimulating the at least one respiratory muscle with the electrode combination, b) using the recruitment relationship, determining an expected respiratory muscle response to the stimulation, and c) comparing an actual respiratory muscle response to the expected respiratory muscle response.

23. The method of claim 21, wherein determining the recruitment relationship includes determining a charge causing zero recruitment of a respiratory nerve that activates the at least one respiratory muscle.

24. The method of claim 23, wherein the respiratory nerve is a phrenic nerve.

25. The method of claim 21, wherein the at least one respiratory muscle includes a diaphragm.

26. The method of claim 21, wherein the method further comprises positioning a first portion of the plurality of electrodes proximate a left phrenic nerve and positioning a second portion of the plurality of electrodes proximate a right phrenic nerve.

27. The method of claim 26, wherein the electrode combination is a first electrode combination, and the plurality of breaths is a first plurality of breaths, and the method further includes repeating the emitting step, the measuring step, and the determining step with a second electrode combination during a second plurality of breaths.

28. The method of claim 27, wherein the first portion of the plurality of electrodes includes the first electrode combination, and the second portion of the plurality of electrodes includes the second electrode combination.

29. The method of claim 21, wherein determining a recruitment relationship includes calculating a line of best fit for a set of data points, and where each data point of the set of data points represents a respiratory muscle response to a corresponding charge.

30. The method of claim 21, wherein determining a recruitment relationship includes calculating a line of best fit for a set of data points, and where each data point of the set of data points represents an average of respiratory muscle responses to corresponding charges.

31. The method of claim 22, wherein the expected respiratory muscle response is no response.

32. The method of claim 22, further comprising, if the actual respiratory muscle response differs from the expected respiratory muscle response, halting stimulation of the at least one respiratory muscle with the electrode combination and re-executing the steps of emitting a plurality of stimulation pulses, measuring respiratory muscle responses, determining the first range and the second range, and developing the recruitment relationship.

33. The method of claim 22, further comprising, at preset time intervals, halting stimulation of the at least one respiratory muscle with the electrode combination and re-executing the steps of emitting a plurality of stimulation pulses, measuring respiratory muscle responses, determining the first range and the second range, and developing the recruitment relationship.

* * * * *

UNITED STATES PATENT AND TRADEMARK OFFICE
CERTIFICATE OF CORRECTION

PATENT NO. : 11,311,730 B2
APPLICATION NO. : 16/510403
DATED : April 26, 2022
INVENTOR(S) : Hoffer et al.

It is certified that error appears in the above-identified patent and that said Letters Patent is hereby corrected as shown below:

In the Specification

Column 1, Line 10:
Delete "which" and insert --which is--.

In the Claims

In Claim 21, Column 26, Line 44:
Delete "change" and insert --charge--.

Signed and Sealed this
Twenty-first Day of June, 2022

Katherine Kelly Vidal
*Director of the United States Patent and Trademark Office*